US012599528B2

(12) United States Patent
Walkington et al.

(10) Patent No.:  US 12,599,528 B2
(45) Date of Patent:      Apr. 14, 2026

(54) UNICONDYLAR BALANCER AND METHOD

(71) Applicant: DEPUY IRELAND UNLIMITED COMPANY, County Cork (IE)

(72) Inventors: Mathew Walkington, Elland (GB); Sheetal Sanak, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 248 days.

(21) Appl. No.: 18/683,913

(22) PCT Filed: Aug. 17, 2022

(86) PCT No.: PCT/EP2022/072922
§ 371 (c)(1),
(2) Date: Feb. 15, 2024

(87) PCT Pub. No.: WO2023/021069
PCT Pub. Date: Feb. 23, 2023

(65) Prior Publication Data
US 2024/0342036 A1      Oct. 17, 2024

(30) Foreign Application Priority Data

Aug. 17, 2021      (GB) ..................................... 2111783

(51) Int. Cl.
*A61G 13/12*          (2006.01)
*A61B 17/02*          (2006.01)
(Continued)

(52) U.S. Cl.
CPC ........ *A61G 13/1245* (2013.01); *A61B 17/155* (2013.01); *A61B 2017/0268* (2013.01); *A61B 2090/064* (2016.02)

(58) Field of Classification Search
CPC ................ A61B 17/025; A61B 17/155; A61B 2017/0268; A61B 2090/061;
(Continued)

(56) References Cited

U.S. PATENT DOCUMENTS 4,501,266 A      2/1985   McDaniel
4,566,448 A      1/1986   Rohr, Jr.
(Continued)

FOREIGN PATENT DOCUMENTS

EP          1276424 A1      1/2003
EP          1276424 B1 *  12/2004   ........... A61B 17/155
(Continued)

OTHER PUBLICATIONS

International Preliminary Report on Patentability From Corresponding PCT/EP2022/072922, Dated Feb. 29, 2024, 9 Pages.
(Continued)

*Primary Examiner* — Scott Luan

(57)          ABSTRACT

A unicondylar balancer (10) for knee surgery and a method of knee surgery. The balancer includes a first body portion (6) including a first jaw (2). The balancer also includes a second body portion (8) slideably attached to the first body portion, the second body portion comprising second jaw (4). The balancer further includes an adjustment mechanism selectively to distance the first jaw from the second jaw. The adjustment mechanism includes a threaded collar (20) captured in a slot (26) in the second body portion, and a threaded rod (30). The first body portion is coupled to the threaded rod via a biasing element (50), which biases the first jaw away from the second jaw. The balancer further includes a manually operable locking mechanism (140), to lock the first body portion with respect to the second body portion.

20 Claims, 10 Drawing Sheets

(51) Int. Cl.
 *A61B 17/15*     (2006.01)
 *A61B 90/00*     (2016.01)

(58) Field of Classification Search
 CPC ...... A61B 2090/064; A61F 2002/3895; A61G
              13/1245
 See application file for complete search history.

(56)      References Cited

U.S. PATENT DOCUMENTS

| | | | |
|---|---|---|---|
| 5,213,112 | A | 5/1993 | Niwa |
| 5,669,914 | A | 9/1997 | Eckhoff |
| 5,911,723 | A | 6/1999 | Ashby |
| 8,551,023 | B2 | 10/2013 | Sherman |
| 11,068,822 | B2 | 7/2021 | Disilvestro |
| 2002/0156480 | A1 | 10/2002 | Overes |
| 2006/0241569 | A1 | 10/2006 | Disilvestro |
| 2009/0198240 | A1 | 8/2009 | Kaufman |
| 2018/0177612 | A1 | 6/2018 | Trabish et al. |

FOREIGN PATENT DOCUMENTS

| | | |
|---|---|---|
| EP | 1645229 A1 | 4/2006 |
| JP | 2017080569 A | 5/2017 |
| WO | 1996017552 A1 | 6/1996 |

OTHER PUBLICATIONS

PCT Search Report From Corresponding PCT/EP2022/072922, Dated Nov. 9, 2022, 3 Pages.

* cited by examiner

UNICONDYLAR BALANCER AND METHOD

CROSS-REFERENCE TO RELATED APPLICATIONS

This application is a national stage entry under 35 U.S.C. § 371 (b) of PCT International Application No. PCT/EP2022/072922, entitled "Unicondylar Balancer and Method" and filed on Aug. 17, 2022, which claims priority to Great Britain Patent Application No. 2111783.3, filed on Aug. 17, 2021, the entire disclosures of both of which are expressly incorporated herein by reference.

BACKGROUND

The present specification relates to a unicondylar balancer for use in knee surgery and to a method of knee surgery.

In both unicompartmental knee arthroplasty (UKA) and total knee arthroplasty (TKA) there may be a need to assess the distraction force in the joint space. This is conventionally done using a sprung platform that displaces due to joint tension or a mechanism utilising a torque handle to apply a known amount of force to distract the joint.

The torque handle design utilises force as a driver for the distraction of the joint and does not allow the user to balance distraction height with force.

Sprung balancers can allow the user to gradually apply further compression to the spring, noting the distraction force and observing the resultant distraction.

U.S. Pat. No. 5,669,914 A describes a rotation alignment device for aligning the tibia with the femur of a patient prior to placement of prosthetic knee components.

U.S. Pat. No. 4,501,266 A describes a knee distraction device for facilitating knee arthroplasty. An adjustable force calibration mechanism is disposed in the device to accommodate controlled selection of the ligament-tensioning force to be applied at respective opposite sides of the knee. The tensioning force can be provided by a screw-threaded connection with a calibrated compression spring interposed between the tensioning members. Fluid pressure can be applied by means of a calibrated pressure valve to apply the ligament-tensioning force.

US 2002/156480 A1 describes spreader apparatuses for knee joints, which are shown to have two parallel support plates which can be inserted between the femur condyles and the tibia and which can be moved apart in connected form by an adjustment mechanism. The adjustment mechanism has a housing at which a stroke-extending tappet is supported via an elastically resilient transmission member in order to simultaneously make the effective spreading travel readable on a scale at the housing and the amount of the spreading force readable on a scale at the housing.

U.S. Pat. No. 5,911,723 A describes a surgical tensioning apparatus that has a base, first and second bone tissue engaging elements mounted on the base and being displaceable toward and away from each other. One of the tissue engaging elements being adapted to be oriented by the tissue engaged thereby. A guide element is provided which is adjustable in relation to the base and one of the tissue engaging elements for positioning first location element to locate a cutting guide provided with cooperating second location element onto the bone to be resectioned.

US 2006/241569 A1 describes an apparatus for use in performing an orthopaedic surgical procedure on a patient that includes at least one femoral paddle and a tibial paddle. At least one of the femoral paddle and the tibial paddle is movable away from the other. The apparatus also includes a sensor configured to generate a signal indicative of a force applied to the femoral paddle or the tibial paddle. The apparatus may be communicatively coupled to a computer assisted orthopaedic surgery system.

WO 1996/017552 A1 describes a bicompartmental tensiometer for use in prosthetic knee surgery, and in particular for use in revision knee surgery. The teniometer comprises two parallel, independently operable jaws which are inserted between resected surfaces on the distal femur and the proximal tibia. The jaws are opened manually by the surgeon until the proper tension is placed on the collateral ligaments. Each of the jaws comprises two paddles which remain parallel, or in the same angular orientation, to each other as they are opened. Moreover, the two jaws remain parallel, or in the same angular orientation, to each other when adjusted for placement adjacent the condyle. Each jaw is held open by a pawl that engages a rack.

U.S. Pat. No. 5,213,112 A describes a tension meter for measuring the degree of tension between bones has a grip portion, a tension meter body mounted to the grip portion, and a torque setting device rotatably connected through a torque shaft to the tension meter body. The tension meter body includes a body portion, a fixed arm extending from one end of the body portion, and a movable arm mounted on the body portion so as to be movable away therefrom. The movable arm is located in opposed relationship to the fixed arm. The movable arm is provided with a gear portion meshing the torque shaft. The torque setting device is provided with a torque limiter for limiting relative displacement of the movable arm in relation to the fixed arm according to a force to be applied between the fixed arm and the movable arm.

US 2009/198240 A1 describes a femoral tibial spreader for spreading adjacent bones that includes a radial measurement gauge for providing incidia corresponding to an amount of force being applied to the forward ends of the femoral tibial spreader. The femoral tibial spreader may be used, for example, to separate the femur and tibia during knee surgery. The radial measurement gauge may be used to determine an amount of force being applied to the femur and tibia, for example, by the medial and arterial ligaments. Two handle members are squeezed together, which causes the forward ends to open. A biasing member allows a measurement extension to pivot towards a handle member under tension, thereby providing a measurement of force applied by the ligaments.

JP 2017/080569 describes a balancer device that comprises a tibia fitting part, a femur fitting part, and a movement mechanism for moving the femur fitting part relative to the tibia fitting part in a direction perpendicular to a proximal end surface of a tibia. The movement mechanism comprises a fixed part fitted to the tibia fitting part, a movable part fitted to the femur fitting part and the fixed part, and a lock mechanism for locking the movable part to the fixed part by a mechanically determined increment. The movable part can extend and contract to move the femur fitting part relative to the tibia fitting part. The movable part has an upper body portion and a turning portion rotatably fitted to the upper body portion and fixed to the femur fitting part. The balancer device also comprises a scale representing the angular position of the turning portion relative to the upper body portion.

SUMMARY

Aspects of the present disclosure are set out in the accompanying independent and dependent claims. Combinations of features from the dependent claims may be combined with features of the independent claims as appropriate and not merely as explicitly set out in the claims.

According to an aspect of the present disclosure, there is provided a unicondylar balancer for use in knee surgery, comprising:

a first body portion including a first jaw for contacting a femoral condyle of a patient;

a second body portion slideably attached to the first body portion, the second body portion comprising second jaw for contacting a tibial plateau of the patient;

an adjustment mechanism for moving the first body portion relative to the second body portion selectively to distance the first jaw from the second jaw, wherein the adjustment mechanism comprises:

a threaded collar captured in a slot in the second body portion; and a threaded rod received through the threaded collar;

wherein the first body portion is coupled to the threaded rod via a biasing element, wherein the biasing element biases the first jaw away from the second jaw;

a plurality of first markings located on the first and second body portions for reading off a distance between a femoral condyle contacting surface of the first jaw and a tibial plateau contacting surface of the second jaw; and a manually operable locking mechanism, separate from the adjustment mechanism, to lock the first body portion with respect to the second body portion selectively to prevent movement of the first jaw with respect to the second jaw against the action of the biasing element.

According to an aspect of the present disclosure, there is provided a unicondylar balancer for use in knee surgery, comprising:

a first body portion including a first jaw for contacting a femoral condyle of a patient;

a second body portion slideably attached to the first body portion, the second body portion comprising second jaw for contacting a tibial plateau of the patient;

an adjustment mechanism for moving the first body portion relative to the second body portion selectively to distance the first jaw from the second jaw, wherein the adjustment mechanism comprises:

a threaded collar captured in a slot in the second body portion; and a threaded rod received through the threaded collar;

wherein the first body portion is coupled to the threaded rod via a biasing element, wherein the biasing element biases the first jaw away from the second jaw; and a manually operable locking mechanism, separate from the adjustment mechanism, to lock the first body portion with respect to the second body portion selectively to prevent movement of the first jaw with respect to the second jaw against the action of the biasing element.

According to another aspect of the present disclosure, there is provided a method of knee surgery, the method comprising:

using a unicondylar balancer, comprising:

a first body portion including a first jaw for contacting a femoral condyle of a patient;

a second body portion slideably attached to the first body portion, the second body portion comprising second jaw for contacting a tibial plateau of the patient;

an adjustment mechanism for moving the first body portion relative to the second body portion selectively to distance the first jaw from the second jaw, wherein the adjustment mechanism comprises:

a threaded collar captured in a slot in the second body portion; and a threaded rod received through the threaded collar;

wherein the first body portion is coupled to the threaded rod via a biasing element, wherein the biasing element biases the first jaw away from the second jaw;

a plurality of first markings located on the first and second body portions for reading off a distance between a femoral condyle contacting surface of the first jaw and a tibial plateau contacting surface of the second jaw; and a manually operable locking mechanism, separate from the adjustment mechanism, to lock the first body portion with respect to the second body portion selectively to prevent movement of the first jaw with respect to the second jaw against the action of the biasing element, by:

placing a leg of the patient in a flexion position;

inserting the first and second jaws between a femoral condyle and a tibial plateau of the leg;

operating the adjustment mechanism to move the first body portion relative to the second body portion to distract the femoral condyle from the tibial plateau until an applied force between the first jaw and the second jaw by the biasing element reaches a predetermined force;

using the plurality of first markings to read off a distance between the femoral condyle contacting surface of the first jaw and the tibial plateau contacting surface of the second jaw at said applied force;

placing the leg in an extension position;

inserting the first and second jaws between the femoral condyle and the tibial plateau of the leg;

operating the adjustment mechanism to move the first body portion relative to the second body portion to distract the femoral condyle from the tibial plateau until an applied force between the first jaw and the second jaw by the biasing element reaches said predetermined force;

using the plurality of first markings to read off a distance between the femoral condyle contacting surface of the first jaw and the tibial plateau contacting surface of the second jaw at said applied force; and determining a position of a resection plane in the femur based on the distances read off using the plurality of first markings in the flexion position and the extension position.

According to another aspect of the present disclosure, there is provided a method of knee surgery, the method comprising:

using a unicondylar balancer, comprising:

a first body portion including a first jaw for contacting a femoral condyle of a patient;

a second body portion slideably attached to the first body portion, the second body portion comprising second jaw for contacting a tibial plateau of the patient;

an adjustment mechanism for moving the first body portion relative to the second body portion selectively to distance the first jaw from the second jaw, wherein the adjustment mechanism comprises:

a threaded collar captured in a slot in the second body portion; and a threaded rod received through the threaded collar;
wherein the first body portion is coupled to the
threaded rod via a biasing element, wherein the
biasing element biases the first jaw away from the
second jaw;
and
a manually operable locking mechanism, separate from
the adjustment mechanism, to lock the first body
portion with respect to the second body portion
selectively to prevent movement of the first jaw with
respect to the second jaw against the action of the
biasing element, by:
placing a leg of the patient in a flexion position;
inserting the first and second jaws between a tibial plateau
and a selected femoral condyle of the leg, the selected
femoral condyle being only one of a medial femoral
condyle and lateral femoral condyle of the leg;
operating the adjustment mechanism to move the first
body portion relative to the second body portion to
distract the femoral condyle from the tibial plateau until
an applied force between the first jaw and the second
jaw by the biasing element reaches a desired force;
determining a distance between the selected femoral
condyle contacting surface of the first jaw and the tibial
plateau contacting surface of the second jaw at said
desired force;
placing the leg in extension;
inserting the first and second jaws between the selected
femoral condyle and the tibial plateau of the leg;
operating the adjustment mechanism to move the first
body portion relative to the second body portion to
distract the selected femoral condyle from the tibial
plateau until an applied force between the first jaw and
the second jaw by the biasing element reaches the
desired force;
determining a distance between the selected femoral
condyle contacting surface of the first jaw and the tibial
plateau contacting surface of the second jaw at said
desired force; and
determining a position of a resection plane in the femur
based on the distances read off using the plurality of
first markings in the flexion position and the extension
position.

Embodiments of this disclosure can provide a convenient
and effective way to measure a distance/spacing between a
selected femoral condyle and a tibial plateau of a leg of a
patient in the flexion and extension positions, and of assess-
ing a distraction force between the selected femoral condyle
and the tibial plateau. In the unlocked configuration of the
locking mechanism, the jaws of the unicondylar balancer
can be moved relative to each other (either by sliding the
first body portion relative to the second body portion, or by
compressing the jaws against the action of the biasing
element), allowing distance measurements to be made and/
or an assessment of the distraction force to be performed.

In some embodiments, the plurality of first markings can
be used to read off the distance/spacing between the selected
femoral condyle and the tibial plateau of the leg (in flexion
and extension positions of the leg) at a given distraction
force between the selected femoral condyle and the tibial
plateau (which may correspond to the force applied to the
jaws by the biasing element). Accordingly, the distance/
spacing between the femoral condyle and the tibial plateau
of the leg may be read off using the plurality of first
markings at a desired (e.g. surgeon selected) distraction
force. The distances measured in the flexion and extension
positions may be used to determine a position of an appropriate resection plane in the femur for mounting a prosthetic
implant on the femur, to achieve the predetermined distrac-
tion force in both the flexion and extension positions once
the prosthetic has been installed. For instance, this may
involve determining the difference between the distance read
off in the flexion position and the distance read off in the
extension position.

In some embodiments, one or more sensors or sensor
arrays can be used to determine the distance/spacing
between the femoral condyle and the tibial plateau of the leg
(in flexion and extension positions of the leg) at a given
distraction force. One example of sensors that may be used
to determine the distance is shown and described in U.S. Pat.
No. 11,068,822, which is expressly incorporated herein by
reference. Such sensors may provide an electrical signal to
a controller, which is configured to display the distance on
a visual display.

The locked down configuration of the locking mechanism
can be used (when not assessing the distraction force) to
simplify the act of reading off the distance between the
femoral condyle and the tibial plateau. For instance, in the
locked down configuration, the inability of the jaws to move
against the action of the biasing element can prevent incor-
rect distance readings from being taken, associated with
movement (expansion) of the (no longer compressed) jaws
when the unicondylar balancer is removed from the leg to
read off the distance using the plurality of first markings. In
some embodiments, the locked down configuration may also
prevent movement of the jaws using the adjustment mecha-
nism, to prevent inadvertent movement of the jaws by
rotation of the threaded collar as the unicondylar balancer is
removed from the leg.

In some embodiments, determining that the force applied
between the first jaw and the second jaw by the biasing
element in the flexion position and/or the extension position
has reached the predetermined force may include manually
moving the unicondylar balancer in a direction perpendicu-
lar to the applied force, to receive tactile feedback regarding
frictional forces applied to the jaws by the selected femoral
condyle and the tibial plateau.

In some embodiments, the unicondylar balancer may
further include a plurality of second markings for reading off
the force applied between the first jaw and the second jaw by
the biasing element. In such embodiments, the method may
further include using the plurality of second markings to
determine that the force applied between the first jaw and the
second jaw by the biasing element in the flexion position
and/or the extension position has reached the predetermined
force.

In some embodiments, a force sensor may be positioned
between the selected femoral condyle and the tibial plateau.
One example of a force sensor is a pressure sensor array, as
shown and described in U.S. Pat. No. 8,551,023, which is
expressly incorporated herein by reference. Such force sen-
sors may provide an electrical signal to a controller, which
is configured to display the applied force on a visual display.

The unicondylar balancer may further include a shaft
extending substantially parallel to the threaded rod. The
shaft may be affixed to, or be integral with, the threaded rod.
The shaft may be slideably mounted through an aperture in
the first body portion. The shaft may provide additional
structural solidity for the coupling between the first and
second body portions.

The biasing element may be a helical spring mounted on
the shaft. A first end of the helical spring may abut a surface of the first body portion at a periphery of the aperture. A second end of the helical spring may abut a surface of the threaded rod.

The shaft may extend from a first end of the threaded rod. The second end of the helical spring may abut the first end of the threaded rod at a periphery of the shaft.

The threaded rod may have a blind axial bore having an opening at a first end of the threaded rod. The shaft may extend from a base of the blind axial bore. The helical spring may abut the base of the blind axial bore at a periphery of the shaft.

The threaded rod of the adjustment mechanism may have a longitudinal axis. The threaded bore may have a longitudinal axis that extends perpendicular to the longitudinal axis of the threaded rod.

In some embodiments, the manually operable locking mechanism may selectively prevent movement of the first jaw with respect to the second jaw against the action of the biasing element while still allowing movement of the first jaw relative to the second jaw under the operation of the adjustment mechanism.

In such embodiments, the manually operable locking mechanism may include a threaded bore in the first body portion, and a threaded screw received within the threaded bore. The threaded screw may be rotatable within the threaded bore to move between a locked position in which an end of the threaded screw urges against the shaft to prevent movement of the first body portion relative to the shaft, and an unlocked position, in which the end of the threaded screw does not contact the shaft. The method may include moving the threaded screw between the unlocked position and the locked position.

In some embodiments, the manually operable locking mechanism may selectively prevent movement of the first jaw with respect to the second jaw against the action of the biasing element while also not allowing movement of the first jaw relative to the second jaw under the operation of the adjustment mechanism.

In such embodiments, the manually operable locking mechanism may include a lever located on the second body portion. The lever may be manually rotatable between a locked position in which an end of the lever is engaged with the first body portion to prevent movement of the first body portion relative to the second body portion, and an unlocked position, in which the end of the lever is disengaged from the first body portion. The method may include manually rotating the lever between the unlocked position and the locked position The first body portion may include a laterally extending protrusion, and the second body portion may include a slot extending parallel to the threaded rod. The end of the lever may be engaged with the laterally extending protrusion when in the locked position.

The lever may be pivotably mounted on the second body portion.

The lever may be integral with the second body portion.

The lever may include a concave surface for aiding manual location and operation of the lever.

The unicondylar balancer may include two of the levers. The levers may be located on opposite lateral sides of the second body portion. The method may include manually rotating each lever between its unlocked position and its locked position.

The unicondylar balancer may further include a guide, which may be removably mountable on the second body portion. The guide may have at least two pin holes for attaching the guide to the femur.

The method may include removably mounting a guide on the second body portion. The guide may include at least two pin holes. The method may also include attaching the guide to the femur by inserting pins through the pin holes and into the femur.

The guide may be a cutting guide having a cutting guide surface. The method may further include resecting the femur using the cutting guide.

The unicondylar balancer may further include a cutting guide. The cutting guide may include a cutting guide surface, and at least two pin holes for attaching the cutting guide to the femur. A spacing and orientation of the pin holes may substantially match a spacing and orientation of the pin holes of the guide mentioned above.

The method may include removing the unicondylar balancer including the guide from the leg of the patient. The method may also include mounting a cutting guide on the femur. The cutting guide may include a cutting guide surface and at least two pin holes. The method may further include resecting the femur using the cutting guide. A spacing and orientation of the pin holes of the cutting guide may substantially match a spacing and orientation of the pin holes of the guide. Mounting the cutting guide on the femur may include inserting the pins through the pin holes of the cutting guide.

According to a further aspect of the present disclosure, there is provided a surgical kit including a unicondylar balancer of the kind set out above.

BRIEF DESCRIPTION OF THE DRAWINGS

Embodiments of this disclosure will be described hereinafter, by way of example only, with reference to the accompanying drawings in which like reference signs relate to like elements and in which.

DETAILED DESCRIPTION

Figure 1:
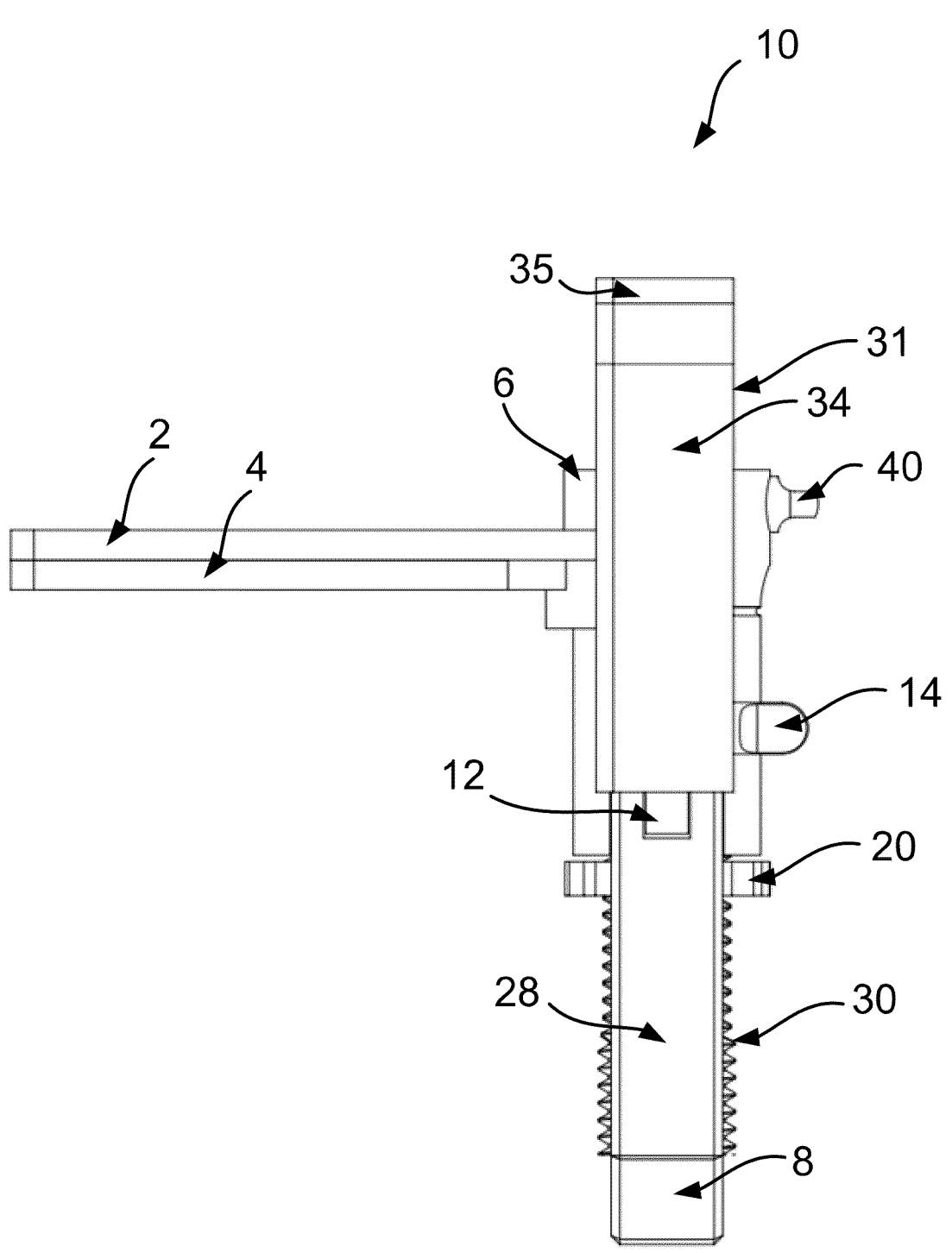
FIG. 1 shows a side view of a unicondylar knee balancer according to an embodiment of this disclosure.
Figure 3:
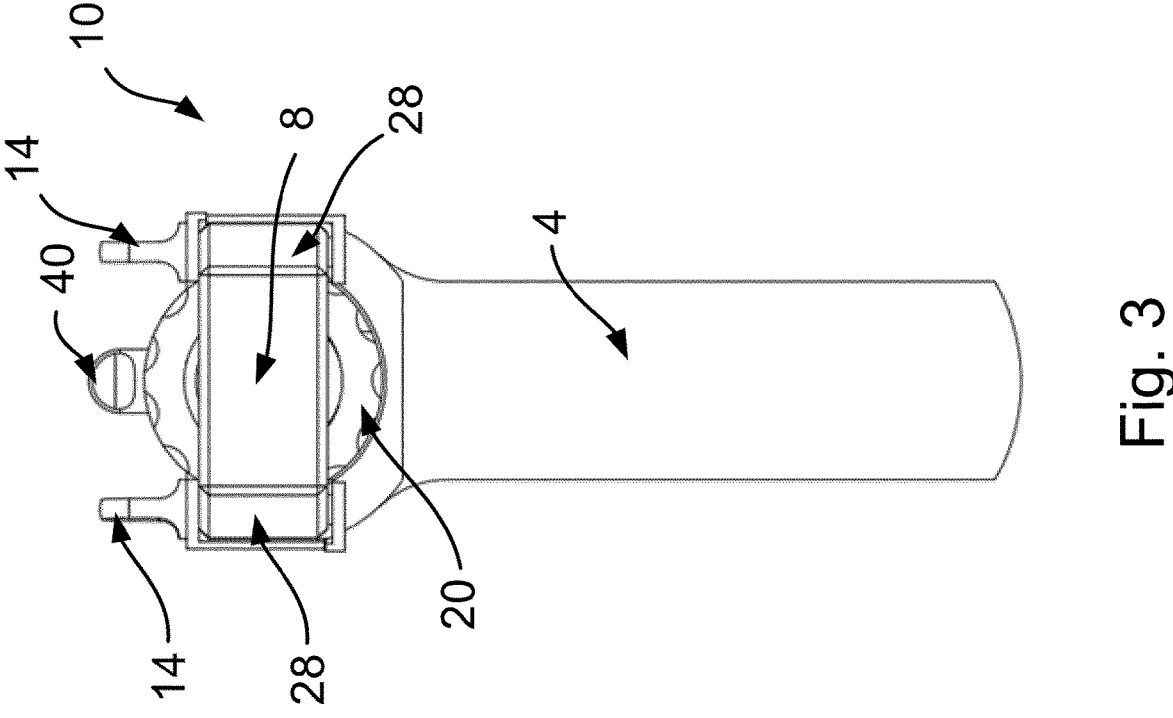
FIG. 3 shows a bottom view of the unicondylar knee balancer of FIG. 1 according to an embodiment of this disclosure.
Figure 2:
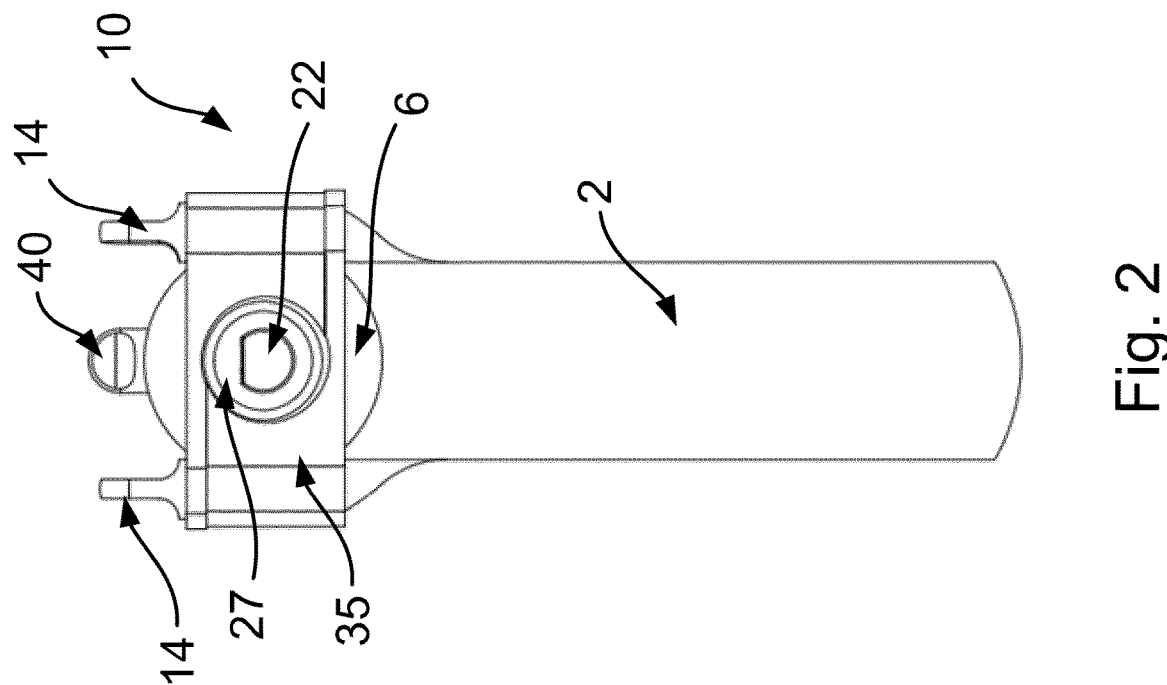
FIG. 2 shows a top view of the unicondylar knee balancer of FIG. 1 according to an embodiment of this disclosure.

Embodiments of this disclosure are described in the following with reference to the accompanying drawings.

Various view of a unicondylar knee balancer 10 according to a first embodiment of this disclosure are shown in FIGS. 1 to 6.

The unicondylar knee balancer 10 includes a first body portion 6 and a second body portion 8. The first body portion 6 includes a first jaw 2 and the second body portion 8 includes a second jaw 4. Each jaw 2, 4 extends substantially orthogonally from its respective body portion 6, 8. In use, the first jaw may be placed in contact with a femoral condyle of a patient, and the second jaw 4 may be placed in contact with a tibial plateau of the patient.

In this embodiment, the second body portion 8 is generally U-shaped, comprising a pair of lateral arms 28 forming the arms of the "U". The first body portion 6 is positioned between the lateral arms 28 of the U-shaped second body portion 8.

The first body portion 6 is slideably attached to the second body portion 8. In this embodiment the second body portion 8 includes slots 17 within which laterally extending protrusions 12 of the first body portion 6 may be slideably received. The slots 17 are provided within the lateral arms 28 of the U-shaped second body portion 8. It will be appreciated that this arrangement may be reversed, so that the first body portion 6 includes slots within which laterally located protrusions (e.g. provided on the lateral arms 28) of the second body portion 8 may be slideably received. Sliding, linear movement of the first body portion 6 relative to the second body portion 8 allows the first jaw 2 and the second jaw 4 to move towards and/or away from each other, so as to allow a surgeon to place the jaws 2, 4 at a desired distance from each other. In particular, the jaws 2, 4, may be adjusted so the first jaw 2 contacts the femoral condyle of the patient and the second jaw 4 contacts the tibial plateau of the patient.

The coupling between the first body portion 6 and the second body portion 8 may also include features for limiting the allowable extent of linear movement between the first body portion 6 and the second body portion 8. In the present embodiment, these features include elongate slots 38 provided in the laterally extending protrusions 12 of the first body portion 6 and a pair of elongate members (e.g. threaded screws) 14 which pass through apertures 15 located in the parts of the second body portion 8 defining the slots 17 and also through the elongate slots 38. The lengths of the elongate slots 38 thus define the maximum extent of the linear movement of the first body portion 6 relative to the second body portion 8, since the elongate members 14 eventually abut the ends of the elongate slots 38 when the laterally extending protrusions 12 slide within the slots 17.

The unicondylar knee balancer 10 may be provided with a plurality of first markings, which allow the surgeon to read off the spacing between the outwardly facing surfaces (namely the surfaces of the jaws which contact the femoral condyle and the tibial plateau of the patient) of the jaws 2, 4. In this way, the surgeon may read off the distance between the femoral condyle and the tibial plateau of the patient, once the first body portion 6 and the second body portion 8 have been slideably positioned to the appropriate location relative to each other. In the present embodiment, the plurality of first markings include markings/indicia 16 (e.g. numerical markings indicating the distance between the outer surfaces of the jaws 2, 4) provided on the second body portion 8. The plurality of first markings in this embodiment also include corresponding marking/indicium 36 is be provided on the first body portion 6. To read off the distance between the outer surfaces of the jaws 2, 4, the surgeon may compare the position of the corresponding marking/indicium 36 with the markings/indicia 16. It will be appreciated that this arrangement may be reversed, such that the markings/indicia 16 are provided on the first body portion 6 and the corresponding marking/indicium 36 is provided on the second body portion 8.

To allow for to controlled movement of the first body portion 6 relative to the second body portion 8, the unicondylar knee balancer 10 is provided with an adjustment mechanism. In this embodiment, the adjustment mechanism includes a threaded collar 20. The threaded collar 20 has an internal thread, which engages with an outer threaded surface of a threaded rod 30, as will be explained in more detail below. The threaded collar 20 may be provided with gripping surfaces (e.g. an outer surface of the threaded collar 20 may be knurled) to facilitate manual rotation of the threaded collar 20 by the surgeon.

The threaded collar 20 is captured in a slot 26 in the second body portion 8. In this embodiment, the slot 26 has two parts, each part being provided in a respective one of the lateral arms 28 of the U-shaped second body portion 8. The slot 26 is inward facing, such that the threaded collar may be held in place between the arms 28 of the U-shaped second body portion 8.

The adjustment mechanism also includes the aforementioned threaded rod 30. The first body portion 6 is coupled to the threaded rod 30. The threaded rod 30 is received through the threaded collar 20 such that rotation of the threaded collar 20 leads to linear movement of the threaded rod 30 in substantially the same orientation as the sliding movement between the first body portion 6 and the second body 8. Owing to the coupling between the threaded rod 30 and the first body portion 6, rotation of the threaded collar 20 results in linear movement of the threaded rod, which in turn leads to linear movement of the first body portion 6 relative to the second body portion 8, for adjusting the positions of the jaws 2, 4.

In this embodiment, the coupling between the threaded rod 30 and the first body portion 6 includes a biasing element 50. The biasing element 50 may, for instance, be a helical spring. The biasing element 50 biases the first body portion 6 away from the second body portion 8, thereby also biasing the first jaw 2 away from the second jaw 4.

In this embodiment, the biasing element 50 is mounted on an elongate shaft 22, such that the shaft 22 passes though the centre of the biasing element 50. The elongate shaft 22 may be considered to be part of the adjustment mechanism, but may also be considered to form part of the manually operable locking mechanism to be described below. The shaft 22 extends substantially parallel to the threaded rod 30. The shaft 22 may be affixed to, or may be integrally formed with the threaded rod 30. An end of the elongate shaft 22 is slideably mounted through an aperture 7 in the first body portion 6, to allow linear movement of the first body portion 6 along the elongate shaft 22 against the action of the biasing element 50. This can allow the jaws 2, 4, to be compressed against the action of the biasing element 50, according to the forces applied on the jaws 2, 4 by the femoral condyle and tibial plateau of the patient's leg as the jaws 2, 4 are moved apart with the unicondylar knee balancer 10 mounted on the leg. The end of the elongate shaft 22 that is slideably mounted through an aperture 7 may be provided with a flange 27 to prevent removal of the elongate shaft 22 from the aperture 7. The flange 27 may be integrally formed with the elongate shaft 22, but in this embodiment, the flange 27 is attached to the elongate shaft 22 by a pin which passes through a bore 25 in the flange 27 and the end of the shaft 22. Note that in the absence of any other forces on the balancer 10, the action of the biasing element 50 urges the first body portion 6 against the underside of the flange 27. Compressing the jaws 2, 4 against the action of the biasing element 50 forces the first body portion 6 away from the flange 27.

Figures 4, 5:
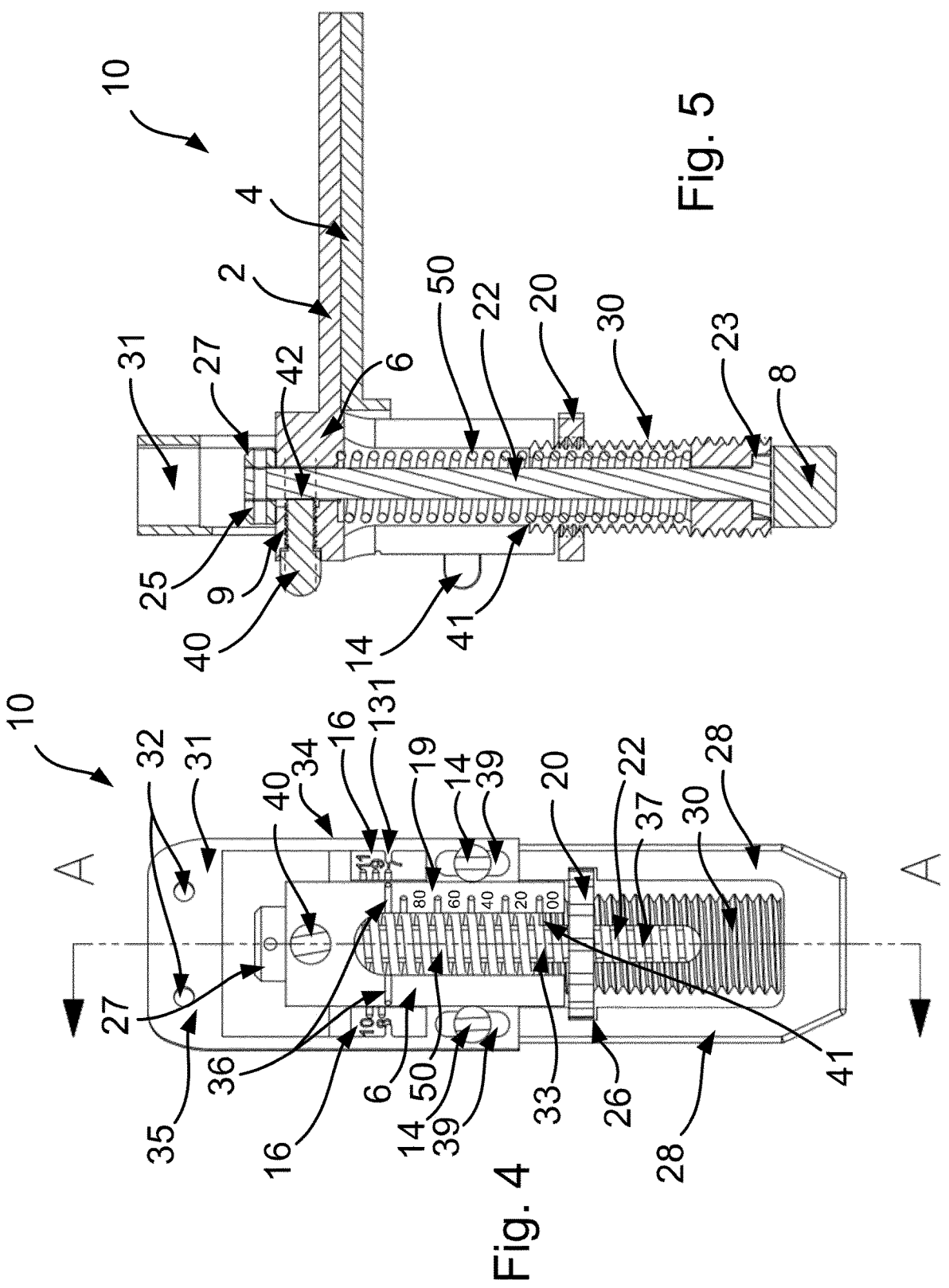
FIG. 4 shows a front view of the unicondylar knee balancer of FIG. 1 according to an embodiment of this disclosure.
FIG. 5 shows a cross section (through the line A-A shown in FIG. 4) of the unicondylar knee balancer of FIG. 1 according to an embodiment of this disclosure.
Figure 6:
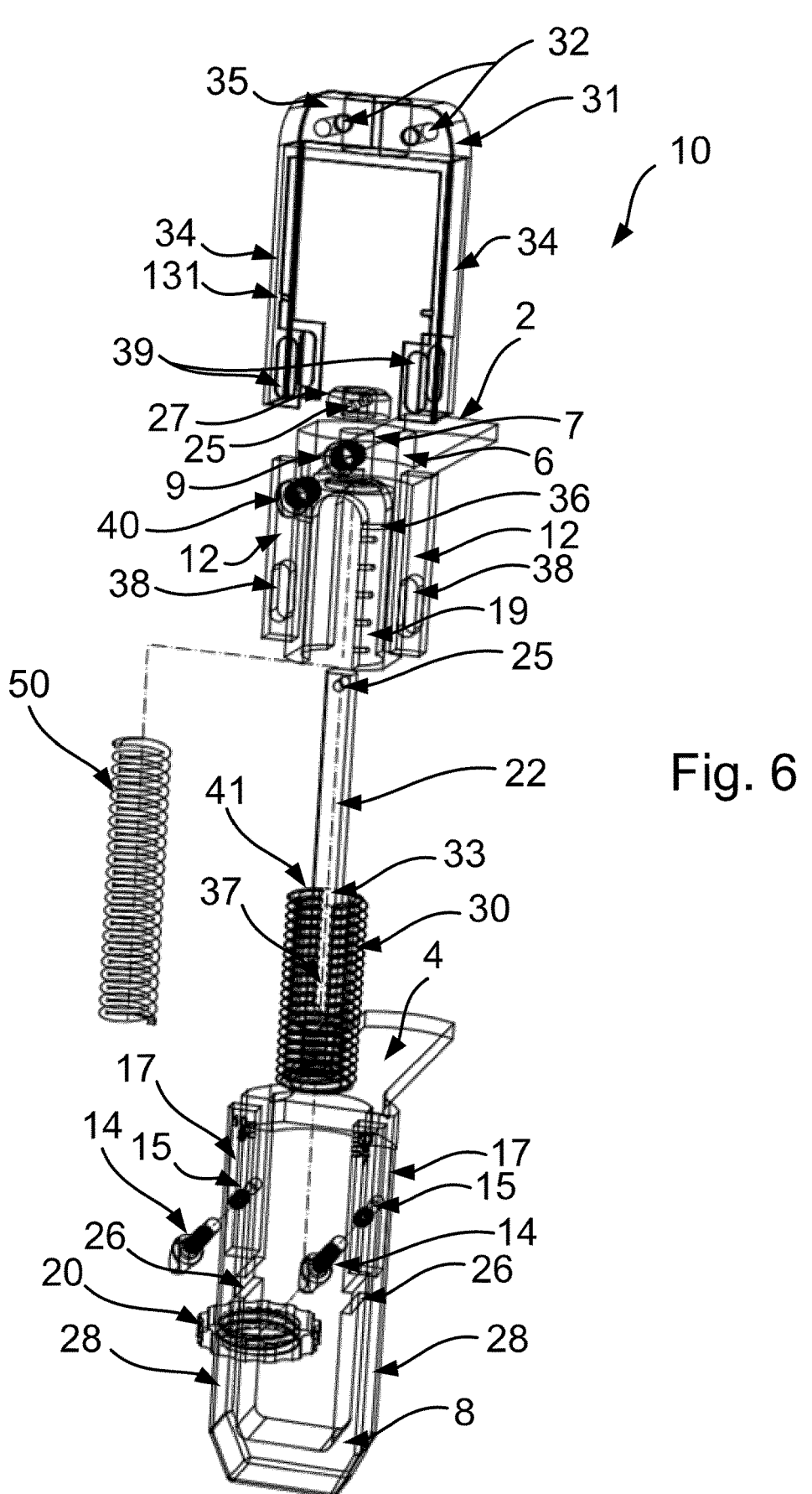
FIG. 6 shows an exploded view of the unicondylar knee balancer of FIG. 1 according to an embodiment of this disclosure.

In this embodiment, a first end of the biasing element 50 abuts a surface of the first body portion 6 at a periphery of the aperture 7 and a second end of the biasing element 50 abuts a surface of the threaded rod 30. In this embodiment, the threaded rod 30 has a blind axial bore 37 having an opening 33 at a first end 41 of the threaded rod 30. The elongate shaft 22 extends from a base of the blind axial bore 37 and the biasing element 50 abuts the base of the blind axial bore 37 at a periphery of the elongate shaft 22. Note that part of the biasing element 50 is thus also located within the blind axial bore 37 in this embodiment. As can be seen in FIG. 5, the end of the elongate shaft 22 which extends from the base of the blind axial bore 37 in this embodiment may pass through a bore in the base of the blind axial bore 37, and may be attached to the base of the blind axial bore 37 by means of a flange 23. As noted above, it is also envisaged that the elongate shaft 22 may be integrally formed with the (e.g. base of the blind axial bore 37 of the) threaded rod 30.

In an alternative embodiment (e.g. in an embodiment of the kind described below in relation to FIGS. 7 to 14), the elongate shaft 22 may extend from a first end of the threaded rod 30. In such embodiments, the end of the biasing element 50 may abut the first end of the threaded rod 30 at a periphery of the elongate shaft 22 where the elongate shaft 22 meets the threaded rod 30.

Accordingly, the adjustment mechanism can provide for movement the first body portion 6 relative to the second body portion 8 selectively to distance the first jaw 2 from the second jaw 4, for example to space the first and second jaws 2, 4 to distract the femoral condyle from the tibial plateau of the patient.

The adjustment mechanism can also allow for an assessment of the distraction force applied by the jaws 2, 4 to the femoral condyle and the tibial plateau of the patient. In particular, the jaws 2, 4 may be compressed against the action of the biasing element 50. The biasing element 50 may provide a spring force against movement of the first jaw 2 and the second jaw 4 towards each other. In this way, the distraction force applied by the jaws 2, 4 to the femoral condyle and tibial plateau of the patient may be adjusted by separating the jaws 2, 4 using the adjustment mechanism as described above.

In this embodiment, the unicondylar knee balancer 10 may be provided with a plurality of second markings for reading off the distraction force on the jaws 2, 4. In the present embodiment, the plurality of second markings comprise markings/indicia 19, which may be in the form of tick marks and/or numerical indications and/or generalized magnitude indications (e.g. "H", "M", "L" for "High", "Medium", "Low") of the distraction force. The markings/indicia 19 may be located on a surface of the first body portion 6. As the biasing element 50 compresses under the distraction force, the first end 41 of the threaded rod 30 moves relative to the first body portion 6, such that the position of the first end 41 of the threaded rod 30 corresponds to the magnitude of the distraction force. With reference to FIG. 4, the distraction force may be read off by noting the position of the first end 41 of the threaded rod 30 against the markings/indicia 19. In the view of the unicondylar knee balancer 10 shown in FIG. 4, the distraction force is at zero, as may seen by the alignment of the first end 41 of the threaded rod 30 with the tick mark 19 denoted "00".

The unicondylar knee balancer 10 is further provided with a manually operable locking mechanism. The manually operable locking mechanism is generally separate (i.e. includes separate components) from the adjustment mechanism. The locking mechanism can be used to lock the first body portion 6 with respect to the second body portion 8, selectively to prevent movement of the first jaw 2 with respect to the second jaw 4 against the action of the biasing element 50.

In this embodiment, the manually operable locking mechanism includes a threaded bore 9 located in the first body portion 6. The threaded bore 9 opens out into the aperture 7. The manually operable locking mechanism in this embodiment also includes a threaded screw 40 received within the threaded bore 9. The threaded bore 9 (and hence the threaded screw 40) has a longitudinal axis that extends perpendicular to the longitudinal axis of the threaded rod 30 of the adjustment mechanism. A proximal end of the threaded screw 40 may be provided with features (e.g. a slot, an Allen key hex or a knurled surface for manual operation) for facilitating the rotation of the threaded screw 40 within the threaded bore 9, such that the threaded screw 40 can be moved back and forth within the threaded bore 9. In this way, the threaded screw 40 can be moved between a locked position, in which a distal end of the threaded screw 40 urges against a sidewall of the elongate shaft 22 received within the aperture 7, and an unlocked position in which the distal end of the threaded screw 40 does not contact the elongate shaft 22.

In the locked position, the urging of the distal end of the threaded screw 40 prevents the first body portion 6 from moving relative to the elongate shaft 22. This prevents the first body portion 6 from moving against the action of the biasing element 50. On the other hand, in the unlocked position, the first body portion 6 is free to slide along the elongate shaft 22 against the action of the biasing element 50, allowing the surgeon to adjust the distraction force on the jaws 2, 4 as the jaws 2, 4 are moved relative to each other.

Accordingly, in this embodiment, the manually operable locking mechanism can allow the surgeon to configure the unicondylar knee balancer 10 in a first configuration in which a distraction force assessment can be made, and a second configuration in which the jaws 2, 4 are held in place relative to the biasing element 50. The second configuration may, for instance, be used when the surgeon wants to measure the distance between the femoral condyle and the tibial plateau of the patient's leg at a given distraction force. For instance, the second configuration can be used when removing the unicondylar knee balancer 10 from the patients leg to inspect the distance between the jaws 2, 4, without the jaws 2, 4 moving under the influence of the biasing element 50.

It is also noted that because the knee joint is generally not rigid and would respond to distracting forces provided by the biasing element 50, in practice, the following two approaches may be used.

In a first approach, the jaws 2, 4 may be driven apart using the adjustment mechanism, until a suitable force is reached according to the markings/indicia 19. At that point, the distance between the jaws 2, 4 may be read off using the markings/indicia 16.

In a second approach, the desired distance between the jaws 2, 4 may be set (by winding the threaded collar 20 until the biasing element 50 is sufficiently compressed to overcome the tension in the knee joint, up until and including the desired separation distance).

In the present embodiment and also in the second embodiment to be described hereinbelow, the locking mechanism may also allow the jaws 2, 4 to be locked down for steady resection.

Note that in this embodiment, when the manually operable locking mechanism is locked down, the spacing of the first and second jaws 2, 4 may still be adjusted using the adjustment mechanism, albeit that movement of the first and second jaws 2, 4 against the action of the biasing element 50 is prevented (this can allow the jaws 2, 4 to be to expanded while disregarding the resisting force). In this embodiment, rotation of the threaded collar 20 leads to linear movement of the first body portion 6, the threaded rod 30, the biasing element 50 and the elongate shaft 22, in unison, relative to the second body portion 8, irrespective of whether or not the manually operable locking mechanism is locked down. The locked down configuration of the manually operable locking mechanism can conveniently allow the surgeon to use the adjustment mechanism to determine the spacing between the femoral condyle and the tibial plateau of the patient without inadvertent movement of the first body portion 6 against the action of the biasing element 50, which may otherwise lead to an incorrect measurement.

The unicondylar balancer 10 in this embodiment may also include a guide 31. This will be described in more detail below, after the description of the embodiment of FIGS. 7 to 14.

Various views of a unicondylar knee balancer 10 according to a second embodiment of this disclosure are shown in FIGS. 7 to 14. The second embodiment shown in FIGS. 7 to 14 shares a number of features in common with the embodiment of FIGS. 1 to 6. In the interests of brevity, while the description of some of the main structural elements of the second embodiment will be repeated, only the significant structural differences between the first and second embodiments will be described in detail.

As with the first embodiment, the unicondylar knee balancer 10 in this embodiment includes a first body portion 6 and a second body portion 8 having respective first and second jaws 2, 4. Again, in this embodiment, the second body portion 8 comprises a pair of laterally located arms 28 forming the arms of a "U", between which the first body portion 6 is positioned.

The first body portion 6 is again slideably attached to the second body portion 8 to allow the outwardly facing surfaces of the jaws 2, 4 to be placed in contact with the femoral condyle and tibial plateau of the patient's leg. In this embodiment the second body portion 8 again includes slots 17 within which laterally extending protrusions 12 of the first body portion 6 may be slideably received. The slots 17 are provided within the lateral arms 28 of the U-shaped second body portion 8. It will again be appreciated that the arrangement for slideably attaching the first body portion 6 to the second body portion 8 may be reversed.

As with the first embodiment, the coupling between the first body portion 6 and the second body portion 8 may include features for limiting the allowable extent of linear movement between the first body portion 6 and the second body portion 8. In the present embodiment, these features include elongate slots 38 provided in the laterally extending protrusions 12 of the first body portion 6 and a pair of elongate members (e.g. pins) 142 which pass through apertures 145 located in the parts of the second body portion 8 defining the slots 17 and also through the elongate slots 38. As will be described below, the elongate members 142 in this embodiment may also be provided for the pivotal mounting of lever of the locking mechanism in this embodiment. The lengths of the elongate slots 38 again define the maximum extent of the linear movement of the first body portion 6 relative to the second body portion 8.

The unicondylar knee balancer 10 may again be provided with a plurality of first markings located on the first and second body portions for reading off a distance between a femoral condyle contacting surface of the first jaw and a tibial plateau contacting surface of the second jaw. In the present embodiment, the plurality of first markings include markings/indicia such as markings/indicia 16 and a corresponding marking/indicium 36 as described above. Again, the positions of the markings/indicia 16 and the corresponding marking/indicium 36 may be reversed, such that the markings/indicia 16 are on the first body portion 6 instead of the second body portion 8 and the marking/indicium 36 is on the second body portion 8 instead of the first body portion 6.

To allow for to controlled movement of the first body portion 6 relative to the second body portion 8, the unicondylar knee balancer 10 is again provided with an adjustment mechanism. In this embodiment, the adjustment mechanism includes a threaded collar 20 captured in a slot 26 in the lateral arms 28 of the second body portion 8, much like in the first embodiment.

In this embodiment, the adjustment mechanism also includes the aforementioned threaded rod 30 received through the threaded collar 20. In this embodiment, the threaded rod 30 is integrally formed with the elongate shaft 22. An end of the elongate shaft 22 is slideably received within an aperture 7 in the first body portion 6, but in the present embodiment, there is no threaded screw 40 received within a threaded bore 9 for locking the first body portion 6 to the elongate shaft 22. As will be described below, locking mechanism in the present embodiment operates differently to the locking mechanism of the first embodiment.

Again, in this embodiment, the threaded rod 30 is received through the threaded collar 20 such that rotation of the threaded collar 20 leads to linear movement of the threaded rod 30 and consequently also the elongate shaft 22, the biasing element 50 (e.g. helical spring) and the first body portion 6 in unison. This allows the adjustment mechanism in this embodiment to be used to set the distance between the jaws 2, 4. The first body portion 6 in this embodiment is coupled to the threaded rod 30 via the elongate shaft 22. In particular, the elongate shaft 22 includes an elongate longitudinal slot 24. A pin 76 passes through an opening 72 in the first body portion and through the elongate slot 24. In this embodiment, the biasing element 50 is again mounted on the elongate shaft 22, and is generally located beneath the pin 76. An upper end of the biasing element 50 engages with, and urges against an interior downward facing surface 147 of the first body part 6 (see FIG. 12). The biasing element 50 thus biases the first body part 6 away from the second body part 8 (thereby also biasing the first jaw 2 away from the second jaw 4). Note that the action of the biasing element 50 in this embodiment thus also biases the pin 76 towards the upper end of the elongate slot 24. In the absence of any compression force on the jaws 2, 4, the pin 76 thus urges against the upper end of the elongate slot 24. When the jaws 2, 4 are compressed under a distraction force, the pin 76 can ride within the slot 24, to allow the first body portion 6 to move relative to the second body portion against the action of the biasing element 50.

Figures 11, 12:
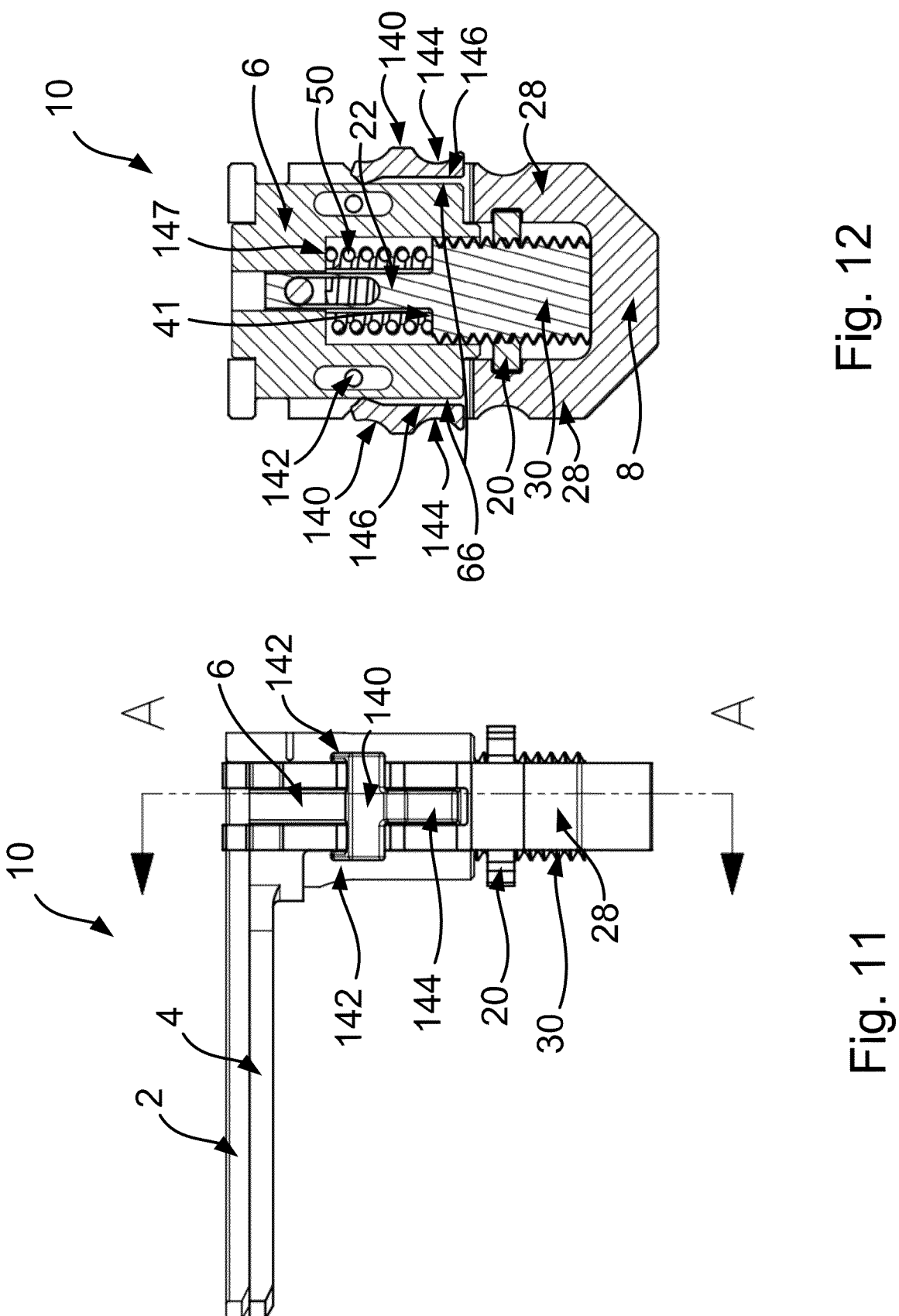
FIG. 11 shows a second side view of the unicondylar knee balancer of FIG. 7 according to an embodiment of this disclosure.
FIG. 12 shows a cross section (through the line A-A shown in FIG. 11) of the unicondylar knee balancer of FIG. 7 according to an embodiment of this disclosure.
Figures 13, 14:
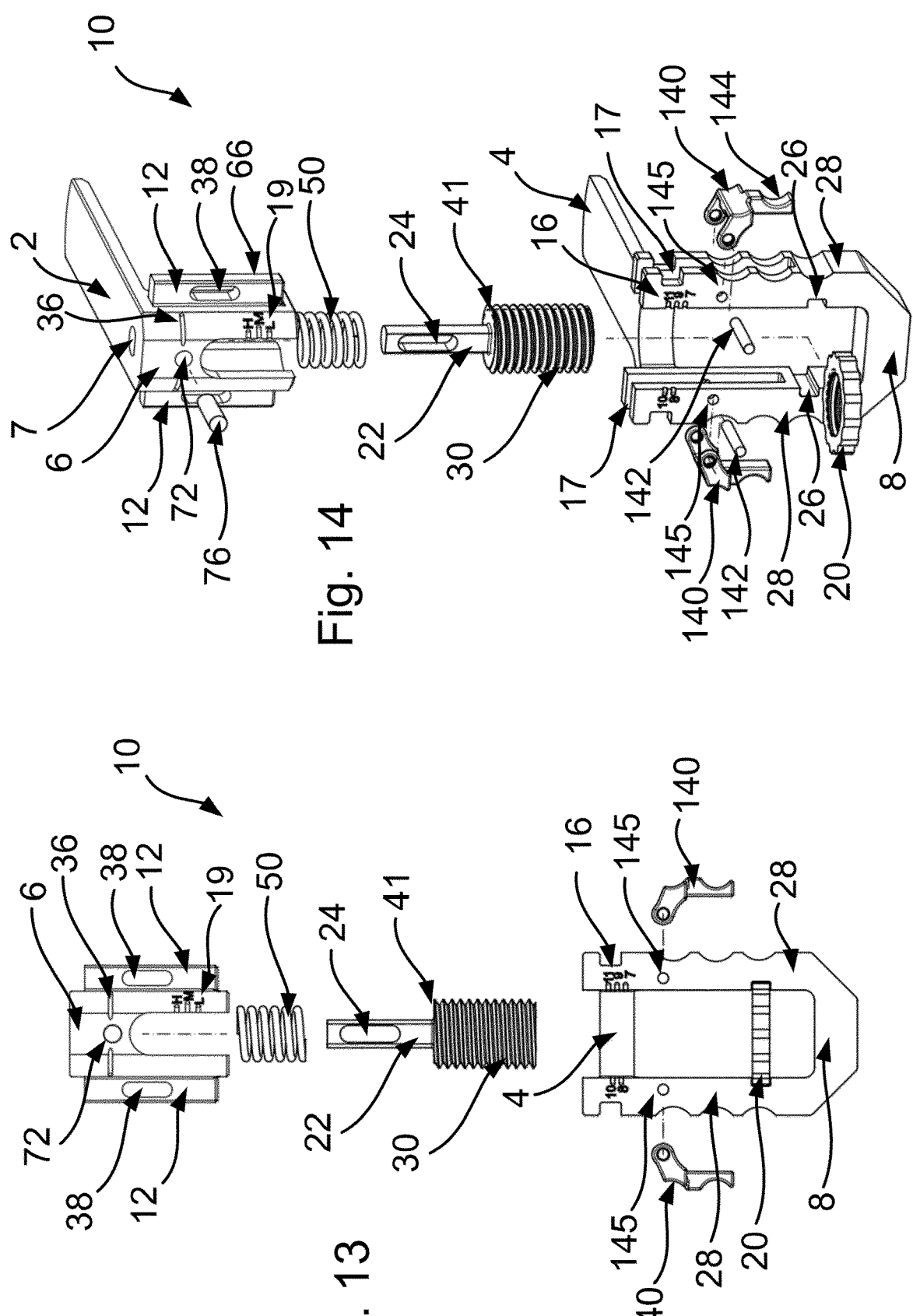
FIGS. 13 and 14 each show an exploded view of the unicondylar knee balancer of FIG. 7 according to an embodiment of this disclosure.

As noted previously, in this embodiment, the elongate shaft 22 may extend from a first end 41 of the threaded rod 30 and an end of the biasing element 50 may abut the first end of the threaded rod 30 at a periphery of the elongate shaft 22 where the elongate shaft 22 meets the threaded rod 30 (i.e. at 41—see FIG. 12).

Accordingly, in this embodiment also, the adjustment mechanism can provide for movement of the first body portion 6 relative to the second body portion 8 selectively to distance the first jaw 2 from the second jaw 4, for example to distract the femoral condyle from the tibial plateau of the patient. Once again, the adjustment mechanism can also allow for an assessment of the distraction force applied by the jaws 2, 4 to the femoral condyle and the tibial plateau of the patient. In particular, the jaws 2, 4 may be compressed against the action of the biasing element 50.

Figures 7, 8:
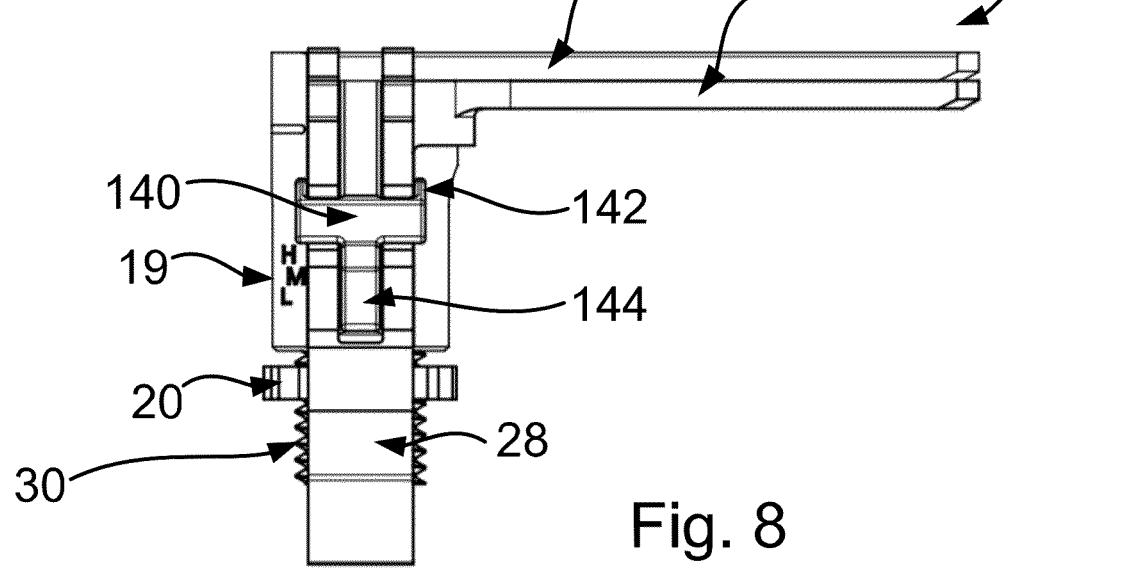
FIG. 7 shows a front view of a unicondylar knee balancer according to another embodiment of this disclosure.
FIG. 8 shows a first side view of the unicondylar knee balancer of FIG. 7 according to an embodiment of this disclosure.
Figures 9, 10:
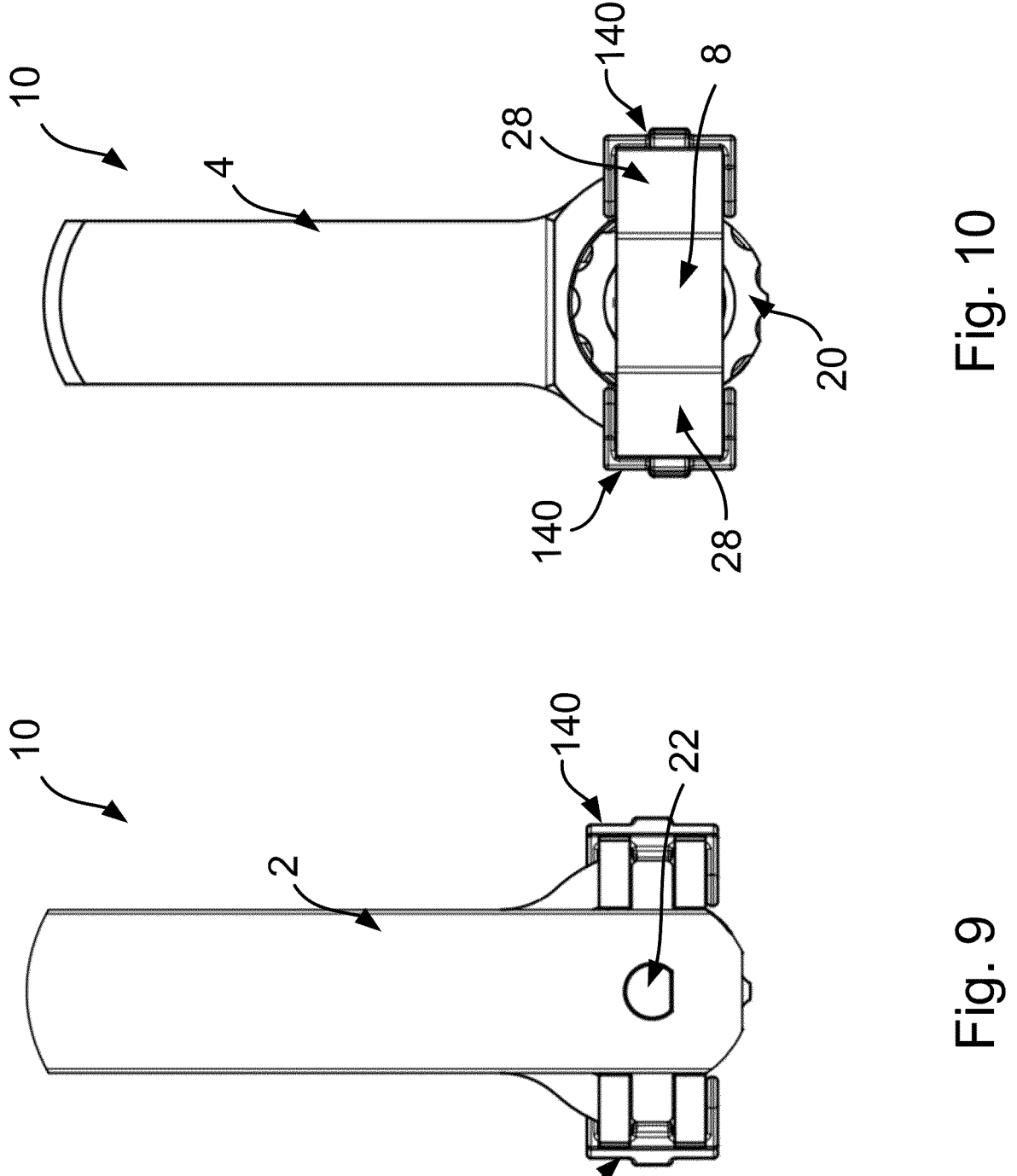
FIG. 9 shows a top view of the unicondylar knee balancer of FIG. 7 according to an embodiment of this disclosure.
FIG. 10 shows a bottom view of the unicondylar knee balancer of FIG. 7 according to an embodiment of this disclosure.

In this embodiment, the unicondylar knee balancer 10 may again be provided with a plurality of second markings for reading off the distraction force on the jaws 2, 4. In the present embodiment, the plurality of second markings comprise markings/indicia 19, which may be in the form of tick marks and/or numerical indications and/or generalized magnitude indications (e.g. "H", "M", "L" for "High", "Medium", "Low") of the distraction force. The markings/indicia 19 may again be located on a surface of the first body portion 6. As the biasing element 50 compresses under the distraction force, the first end 41 of the threaded rod 30 moves relative to the first body portion 6, such that the position of the first end 41 of the threaded rod 30 corresponds to the magnitude of the distraction force. With reference to FIG. 7, the distraction force may be read off by noting the position of the first end 41 of the threaded rod 30 against the markings/indicia 19. In the view of the unicondylar knee balancer 10 shown in FIG. 7, the distraction force is at zero, as may be seen by the alignment of the first end 41 of the threaded rod 30 with the tick mark 19 denoted "L".

Unlike the manually operable locking mechanism of the first embodiment, the manually operable locking mechanism of the present embodiment can be used to lock the first body portion 6 with respect to the second body portion 8, selectively to prevent movement of the first jaw 2 with respect to the second jaw 4 against the action of the biasing element 50, while also preventing movement of the first jaw 2 with respect to the second jaw 4 under the operation of the adjustment mechanism. This can, for example, aid in preventing any movement of the jaws 2, 4 relative to each other (either due to movement under the action of the biasing element 50 or the threaded collar 20) when removing the unicondylar knee balancer 10 from the patient's leg to read off the distance between the jaws 2, 4 using the markings/indicia 19 and marking/indicium 36.

In this embodiment, the manually operable locking mechanism includes one or more levers 140. The present embodiment includes two such levers 140, each provided on a respective lateral arm 28 of the second body portion 8, but it is envisaged that only one such lever 140 could be provided. The or each lever 140 may be integrally formed with the second body portion 8, such that the or each lever 140 can pivot around a point at which the lever 140 meets the second body portion 8. However, in the present embodiment, each lever is pivotally attached to the second body portion 8 using a respective one of the aforementioned pins 142. Each pin 142 may thus pass though openings provided at one end of each lever 140, through the apertures 145 located in the parts of the second body portion 8 defining the slots 17 and also through the elongate slots 38.

The or each lever 140 is manually rotatable to move between a locked position and an unlocked position. The or each lever 140 may be provided with gripping surfaces such as concave surfaces 144, to aid the surgeon in manually operating the lever(s) 140. To move the lever(s) 140 to the locked position, the surgeon may press down on (e.g. the gripping surfaces of) the lever(s) 140. The lever(s) 140 generally reside in their unlocked position when they are not being pressed down by the surgeon.

In the locked position of the or each lever 140, an inward facing surface 146 of the or each lever 140 presses against a surface 66 of the laterally extending protrusions 12 of the first body portion 6 (see FIG. 12), to prevent sliding movement of the laterally extending protrusions 12 within the slots 17 of the second body portion 8. This prevents movement of the first body portion 6 relative to the second body portion 8, either under the action of the adjustment mechanism or against the action of the biasing element 50. In the unlocked position of the lever(s) 140, the inward facing surface 146 of the or each lever 140 does not urge against the surface 66 and indeed may not even contact the surface 66. Accordingly, in the unlocked portion of the lever(s) 140, the first and second body portions 6, 8 can move relative to each other.

In some embodiments, the surfaces 146, 66 may be provided with features to allow "digital locking" of the first body portion 6 in a finite number of discrete vertical positions with respect to the second body portion 8. For example, the surface 66 may be provided with a number of grooves spaced apart at regular intervals, for receipt of a medially facing tooth provided on the surface 146.

The unicondylar balancer 10 in both of the embodiments described above may also include a guide. The guide may be a cutting guide, or may be an intermediate guide, for mounting pins in a bone of the patient's leg, for subsequent mounting of a cutting guide.

Returning to FIGS. 1 to 6, the guide 31 in this embodiment includes a generally U-shaped body having a pair of laterally spaced arms 28 and a base 35. The guide also includes one or more pin holes 32 for inserting pins or screws into a bone (generally the femur) of the patient's leg.

The guide 31 is mountable on the first body part 6 of the unicondylar balancer 10 (e.g. see FIGS. 1 to 4). When mounted, the arms 34 of the guide 31 fit over and embrace the laterally facing sides of the first body portion 6. In the mounted position, an opening in the base 35 of the guide 31 may receive the flange 27 so that a lower edge of the base 35 can rest against an upper surface of the first body portion 6.

The ends of the arms 34 may be provided with slots 39. When the guide 31 is mounted on the first body portion 6, the slots 39 may align with the pair of elongate members (e.g. threaded screws) 14 which pass through apertures 15 located in the parts of the second body portion 8 defining the slots 17 and also through the elongate slots 38. To attach the guide to the unicondylar balancer 10, the elongate members 14 may be removed and then re-inserted through the slots 39, once the guide is in place. The slots 39 allow the first body part 6 to move relative to the second body part 8, while the elongate members 14 ride within the slots 39.

As will be described in more detail below, the guide can be used to position pins or screws into a bone (generally the femur) of the patient's leg, for subsequent mounting of a cutting guide to perform a femoral resection. In particular, with the unicondylar balancer 10 including the guide 31 in position, pins or screws may be inserted thorough the pin holes 32 and into the bone. Thereafter, the unicondylar balancer 10 including the guide 31 may be removed from the patient's leg and the pins or screws inserted through the pinholes of a corresponding cutting guide. Note that the pinholes of the corresponding cutting guide may have a spacing and orientation which substantially matches a spacing and orientation of the pin holes of the guide 31.

The corresponding cutting guide may include a cutting guide surface (e.g. a cutting slot), which has a predetermined spatial relationship with the pin holes of the cutting guide. In this way, having first used the unicondylar balancer 10 including the guide 31 to determine the correct location of the pins or screws for a desired resection plane, the corresponding cutting guide may be attached to the patient's leg using the pins or screws, such that the cutting guide surface aligns with the desired resection plane.

In the embodiment of FIGS. 1 to 6, the guide 31 is an intermediate guide, which may be used to correctly position pins or screws for subsequent attachment of a cutting guide using those pins or screws. It is also envisaged that the guide 31 may itself be a cutting guide, incorporating a cutting guide surface. This may obviate the need to provide a separate cutting guide. An example of such an approach is described below in relation to the embodiment of FIGS. 7 to 14, and with reference to FIGS. 15 to 17.

Figure 17:
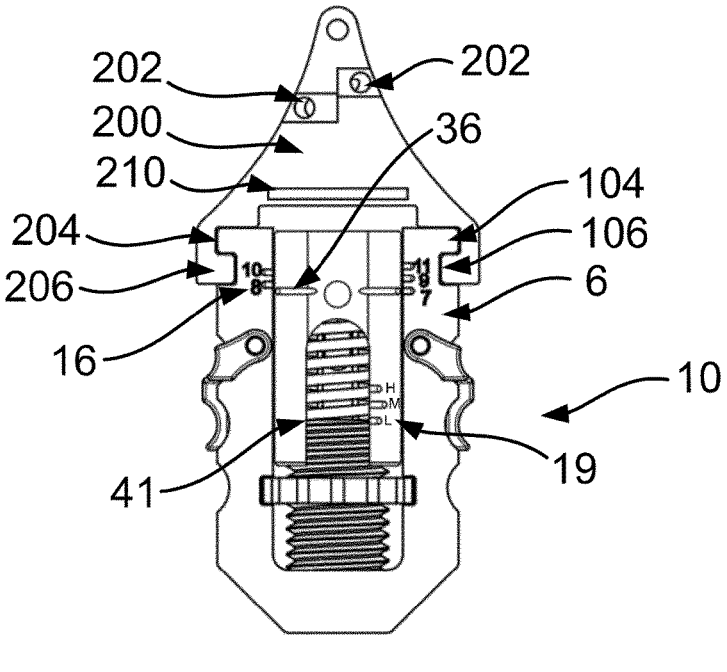
FIG. 17 shows a cutting guide attached to a unicondylar knee balancer of the kind shown in FIGS. 7 to 14 according to an embodiment of this disclosure.

FIG. 17 shows a cutting guide 200 mounted on a unicondylar balancer 10 according to the second embodiment described above. The cutting guide 200 may include a pair of arms including features such as rails 206 and slots 204 for mating with corresponding slots 106 and rails 104 located of the first body portion 6. The cutting guide 200 may thus be slidably mountable on the first body portion 6 such that the rails 104 ride within the slots 204 and such that the rails 206 ride within the slots 106.

The guide includes a plurality of pin holes 202, through which pins or screws may be inserted into a bone (generally the femur) of the patient's leg once the guide 200 is at the correct position. Note that once the pins or screws have been inserted, the unicondylar balancer 10 may be slidably removed, leaving the cutting guide 200 attached to the patient's leg. This can provide more space for the use of the cutting guide 200 and the resection tool while resecting the patient's femur.

The cutting guide 200 also includes a cutting guide surface. The cutting guide surface may be an open surface along which a resection tool can be guided. However, in the embodiment showing in FIGS. 15 to 16, the cutting guide surface is a closed surface comprising in a cutting slot 210, which may provide more control over the resection tool. The cutting guide surface is oriented generally orthogonally with respect to the direction of travel of the first body portion 6 when the first body portion 6 moves with respect to the second body portion 8 under the operation of the adjustment mechanism and/or against the action of the biasing element 50.

Figures 15, 16:
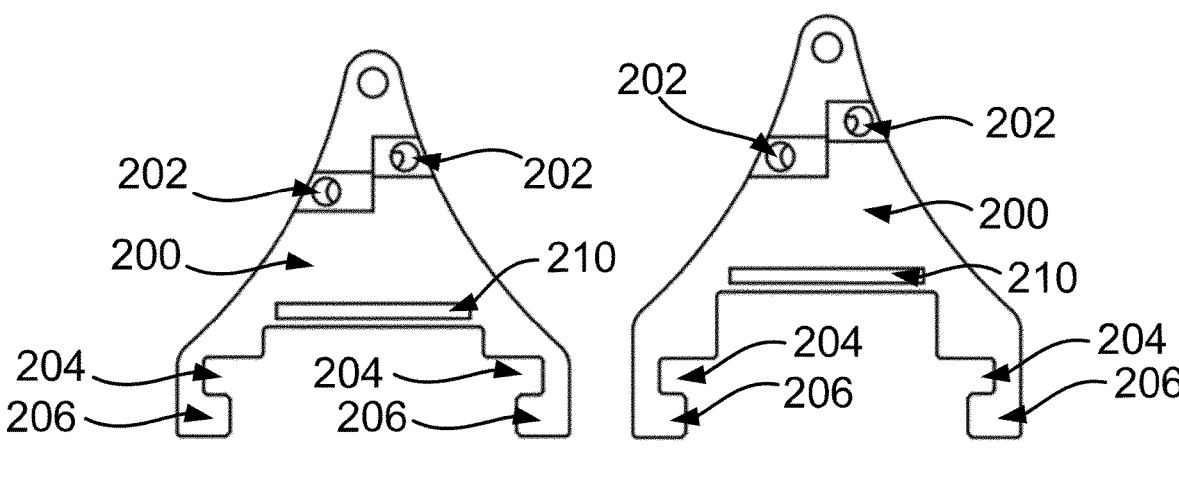
FIGS. 15 and 16 each show a cutting guide according to an embodiment of this disclosure.

It is envisaged that differently sized cutting guides 200 may be provided. FIGS. 15 and 16 show two differently sized cutting guides 200 in accordance with this approach. Note that the main difference between the cutting guides 200 in FIGS. 15 and 16 is that the cutting guide surface (slot 210) in FIG. 16 is located further away from the first body portion 6 when the cutting guide 200 of FIG. 16 is mounted on the first body portion 6 than is the case for the cutting guide 200 of FIG. 15. Appropriate selection of a cutting guide having a certain size can allow the resection plane to be positioned as desired. +

It should be appreciated that, for any of the embodiments of the unicondylar balancer, some or all of the plurality of first markings and the plurality of second markings of the unicondylar balancer may be omitted, and the unicondylar balancer 10 may be used with one or more sensor arrays to determine the distance between the femoral condyle and tibial plateau and/or the force applied between the femoral condyle and tibial plateau, as described in greater detail below.

According to an embodiment of this disclosure, a unicondylar balancer 10 of the kinds described herein may be provided as part of a surgical kit. The surgical kit may include one or more other components for use in knee surgery (for instance a plurality of cutting guides of the kind shown in FIGS. 15 and 16).

Figure 18:
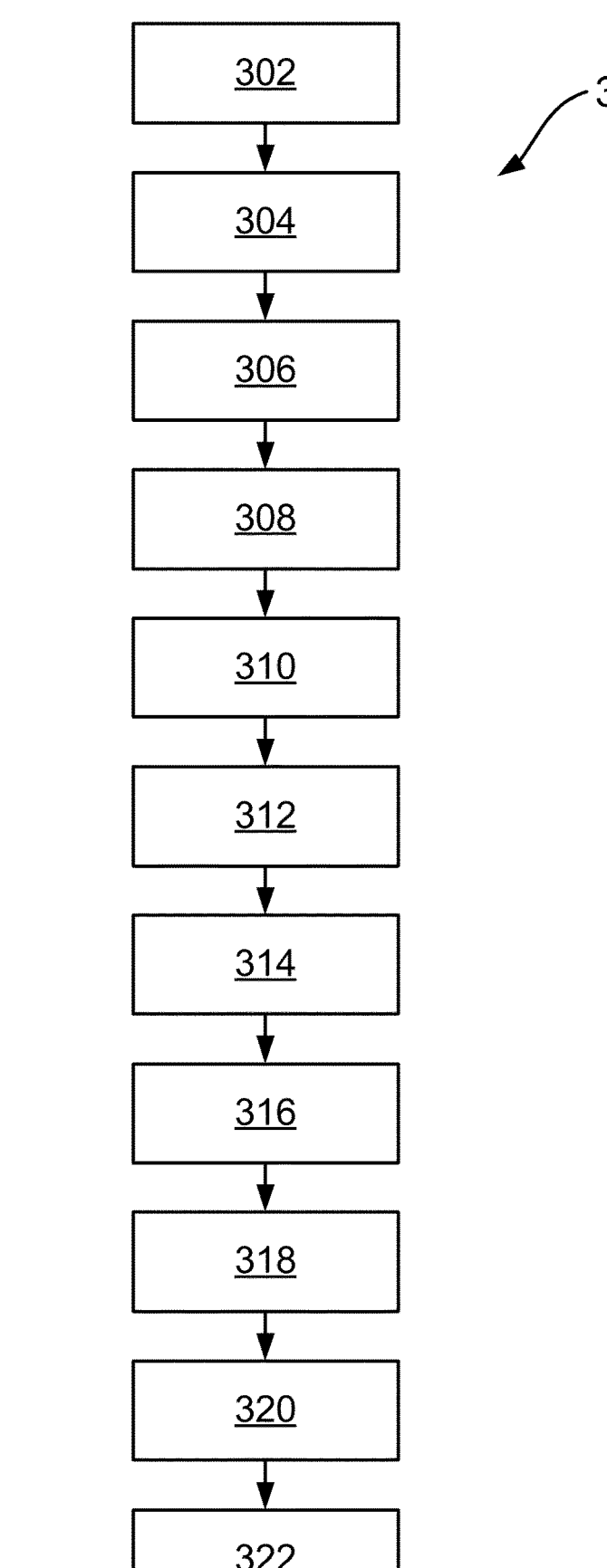
FIG. 18 shows a method of knee surgery according to an embodiment of this disclosure.

FIG. 18 shows a method 300 of knee surgery according to an embodiment of this disclosure.

In a first step 302, the method may involve a number of preparation procedures such as gaining access to the knee joint and providing a unicondylar knee balancer 10 of the kind described above.

In step 304, the leg of the patient is placed in a flexion position.

In step 306, the unicondylar knee balancer 10 is mounted on the patient's leg, by inserting the first and second jaws 2, 4 between the posterior portion of a selected femoral condyle a tibial plateau of the leg. The selected femoral condyle may be only one of a medial femoral condyle and a lateral femoral condyle.

In step 308, the adjustment mechanism is operated, for instance by rotating the threaded collar 20. This moves the first body portion 6 relative to the second body portion 8, which in turn separates the jaws 2, 4 to distract the femoral condyle from the tibial plateau. The jaws 2, 4 may be separated until an applied force between the first jaw 2 and the second jaw 4 by the biasing element 50 reaches a desired force. The desired force may, for instance, be a desired distraction force corresponding to a desired ligament tension determined during pre-operative planning.

The force applied by the biasing element 50 (corresponding to the ligament tension) may be determined in a number of ways.

In one embodiment, the force applied by the biasing element 50 to the jaws 2, 4 may be assessed by moving the unicondylar balancer 10 (e.g. back and forth) in a direction perpendicular to the applied force (e.g. in a medial/lateral and/or anterior/posterior direction), to receive tactile feedback regarding frictional forces applied to the jaws 2, 4 by the femoral condyle and the tibial plateau. In this way, the surgeon may be able to determine that the desired force, associated with the desired ligament tension, has been reached.

In another embodiment, the unicondylar balancer 10 may comprise the previously discussed plurality of second markings (e.g. the markings/indicia 19) for reading off the force applied between the first jaw 2 and the second jaw 4 by the biasing element 50. In such embodiments, the method may involve using the plurality of second markings to determine that the force applied between the first jaw 2 and the second jaw 4 by the biasing element 50 in the flexion position has reached the desired force.

In another embodiment, a force sensor may be positioned between the selected femoral condyle and the tibial plateau. The force sensor may be a pressure sensor array, electronic force sensor, or other sensor capable of measuring compression, such as a piezoelectric sensor, capacitive sensor, load cell, or other force sensor. One example of a capacitive pressure sensor array, as shown and described in U.S. Pat. No. 8,551,023, which is expressly incorporated herein by reference. The force sensor is configured to detect the load applied to the selected femoral condyle and the tibial plateau by the unicondylar balancer and generate an electrical signal that is provided to an external device such as, for example, an electronic controller, a computer, a display, an external interface device, a transceiver, or other devices. The external device may be used to view, store, or otherwise process force data generated by the force sensor. Alternatively, in some embodiments, force sensor may include a wireless communication circuit to communicate with external devices. The force measurement may be placed on the visual display for review by the surgeon.

In step 310, with the jaws 2, 4 having been set, using the adjustment mechanism, to a distance at which the distraction force is substantially equal to the desired force (e.g. corresponding to the desired ligament tension), the surgeon may use the plurality of first markings (e.g. the markings/indicia 16 and the corresponding marking/indicium 36) to read off a distance between the selected femoral condyle contacting surface of the first jaw 2 and the tibial plateau contacting surface of the second jaw 4 at the desired force. As part of this, the locking mechanism may be used. For instance, as described previously, the locking mechanism may be used to lockdown the jaws 2, 4 against movement under the action of the biasing element 50 (and optionally also against movement associated with the threaded collar 20). The locking mechanism may thus improve the accuracy of the distance measurements taken in the flexion position, for instance if the surgeon removes the unicondylar balancer 10 from the patient's leg to inspect the plurality of first markings.

In another embodiment, one or more sensors or sensor arrays may be used to determine the distance between the selected femoral condyle and the tibial plateau. One example of sensors that may be used to determine the distance is shown and described in U.S. Pat. No. 11,068,822, which is expressly incorporated herein by reference. For example, sensor arrays may be coupled to the femur and tibia, and one or more cameras positioned in the operating room. Image data received from the cameras may used to determine the location and orientation of the selected femoral condyle and the tibial plateau, and thereby calculate the distance between the bones. An external device such as, for example, an electronic controller, a computer, a display, an external interface device, a transceiver, or other devices may be used to determine the location and orientation of the bones and view, store, or otherwise process the data. The distance measurement may be placed on the visual display for review by the surgeon.

In step 312, the leg of the patient is placed in an extension position.

In step 314, the unicondylar knee balancer 10 is again mounted on the patient's leg, by inserting the first and second jaws 2, 4 between a distal femoral condyle and a tibial plateau of the leg.

In step 316, the adjustment mechanism is again operated, for instance by rotating the threaded collar 20. This again moves the first body portion 6 relative to the second body portion 8, which in turn separates the jaws 2, 4 to distract the femoral condyle from the tibial plateau. The jaws 2, 4 may be separated until an applied force between the first jaw 2 and the second jaw 4 by the biasing element 50 reaches the desired force (e.g. the desired ligament tension determined during pre-operative planning).

The force applied by the biasing element 50 in the extension position may be determined in a number of ways. For example, either of the two approaches mentioned above (manual movement in a direction perpendicular to the applied force of by using the plurality of second markings) may be used.

In step 318, with the jaws 2, 4 having been set, using the adjustment mechanism, to a distance at which the distraction force is substantially equal to the desired force (e.g. corresponding to the desired ligament tension), the surgeon may again use the plurality of first markings (e.g. the markings/indicia 16 and the corresponding marking/indicium 36) to read off a distance between the femoral condyle contacting surface of the first jaw 2 and the tibial plateau contacting surface of the second jaw 4 at the desired force. As part of this, the locking mechanism may again be used. For instance, as described previously, the locking mechanism may be used to lockdown the jaws 2, 4 against movement under the action of the biasing element 50 (and optionally also against movement associated with the threaded collar 20). The locking mechanism may thus improve the accuracy of the distance measurements taken in the extension position, for instance if the surgeon removes the unicondylar balancer from the patient's leg to inspect the plurality of first markings.

In step 320, the distances read off in steps 310 (leg in flexion) and 318 (leg in extension) may be used to determine a position of a resection plane in the femur.

In particular, the distance measurement taken at the desired ligament tension in step 318 (leg in extension) may be deducted from the distance measurement taken at the desired ligament tension in step 310 (leg in flexion), or indeed vice versa. The result of this calculation can yield the appropriate position of the resection plane on the femur, for achieving the desired ligament tension with the leg both in flexion or extension, once the distal end of the femur has been resected and a prosthetic has been installed to replace the distal end of the femur. In other words, the calculation can be used to determine the distal position, along the femur, of the resection plane upon which the prosthetic will subsequently by installed.

In this regard, and bearing in mind that the prosthetics used in knee surgery may have a standard thickness, note that the resection plane position determines the final location and thus distal extent of an outer surface of the prosthetic to be installed on the femur. The calculation described above may thus allow the distal femur (which faces the tibial plateau when the leg is in extension) to be resected at the correct distal location for positioning the distal outer surface of the installed prosthetic at the correction position for the desired ligament tension in extension. The desired tension in extension may generally match the desired tension in flexion, and it may also be noted that the installation of the prosthetic for replacing the distal end of the femur may have little or no effect upon the interaction (e.g. spacing) between the posterior face of the distal femur and the tibial plateau when the patient's leg is in flexion.

In step 322, resection of the femur may be performed along the resection plane determined in step 320. This may, for instance, be achieved using an intermediate guide 31 of the kind described above in relation to FIGS. 1 to 6, or a cutting guide 200 of the kind described above in relation to FIGS. 15 to 17.

When a unicondylar knee balancer 10 of the kind shown in FIGS. 1 to 6 is used, the intermediate guide 31 may be mounted on the unicondylar knee balancer 10 as noted above, with the leg in the extension position. To position the guide 31, the guide 31 may include a tick mark or other indicium 131, which may be aligned with the plurality of first markings by sliding the guide 31 along the first length of the body part 6 of the unicondylar balancer 10. In particular, the indicium 131 may be aligned with the markings/indicia 16 by first aligning the indicium 131 with the distance read off using the plurality of first markings with the leg in extension (in step 318). Then, the guide 31 may be moved distally (e.g. further toward the threaded collar 20) by an amount determined in the calculation performed in step 320. By way of example, the distance in step 310 (leg in flexion) was determined to be "9" and the distance in step 318 (leg in extension) was determined to be "11", whereby the difference is "2", then the guide 31 may be moved so that the indicium 131 aligns with "9" (="11"–"2") on the markings/indicia 16.

Pins or screws may then be inserted into the anterior surface of the femur through the pin holes 32. The unicondylar balancer 10 including the guide 31 may then be removed from the patient's leg. A cutting guide may then be mounted on the femur using the pins or screws. The cutting guide may comprise a cutting guide surface (e.g. a cutting slot) and a plurality of pin holes having the same shape and layout as the pin holes 32 of the guide 31. The spatial relationship between the pin holes and the cutting guide surface of the cutting guide may be fixed so that the cutting guide surface is in the correct position for resecting the femur according to the measurements and calculations performed using the unicondylar knee balancer 10. The distal end of the femur may next be resected using the cutting guide surface of the cutting guide.

Following resection, the cutting guide and pins or screws may be removed from the patient's leg and the surgical procedure may continue to further steps such as preparation of the femur (including, for example, femoral sizing and further cuts) followed by installation of the prosthetic on the resected surface of the femur.

When a unicondylar knee balancer 10 and cutting guide 200 of the kind shown in FIGS. 7 to 17 is used, a plurality of differently sized cutting guides may normally be provided. The appropriately sized cutting guide is chosen (and then mounted on the unicondylar knee balancer 10 with the leg in the extension position) according to the calculation performed in step 320. By way of example, the distance in step 310 (leg in flexion) was determined to be "9" and the distance in step 318 (leg in extension) was determined to be "11", whereby the difference is "2", then a cutting guide having a cutting guide surface (slot 210) appropriate for the result "2" may be chosen and mounted on the unicondylar knee balancer 10.

Pins or screws may then be inserted into the anterior surface of the femur through the pin holes 202. The unicondylar balancer 10 may optionally then be removed from the patient's leg, leaving the cutting guide 200 in place. The distal end of the femur may next be resected using the cutting guide surface 210 of the cutting guide 200.

Following resection, the cutting guide 200 and pins or screws may be removed from the patient's leg and the surgical procedure may continue to further steps such as preparation of the femur (including, for example, femoral sizing and further cuts) followed by installation of the prosthetic on the resected surface of the femur.

Accordingly, there has been described a unicondylar balancer for knee surgery and a method of knee surgery. The balancer includes a first body portion including a first jaw. The balancer also includes a second body portion slideably attached to the first body portion, the second body portion comprising second jaw. The balancer further includes an adjustment mechanism selectively to distance the first jaw from the second jaw. The adjustment mechanism includes a threaded collar captured in a slot in the second body portion, and a threaded rod. The first body portion is coupled to the threaded rod via a biasing element, which biases the first jaw away from the second jaw. The balancer also includes a plurality of first markings for reading off a distance between the first jaw and the second jaw. The balancer further includes a manually operable locking mechanism, to lock the first body portion with respect to the second body portion.

Although particular embodiments of this disclosure have been described, it will be appreciated that many modifications/additions and/or substitutions may be made within the scope of the claims.

The invention claimed is:

1. A unicondylar balancer for use in knee surgery, comprising:
   a first body portion including a first jaw for contacting a femoral condyle of a patient;
   a second body portion slideably attached to the first body portion, the second body portion comprising second jaw for contacting a tibial plateau of the patient;
   an adjustment mechanism for moving the first body portion relative to the second body portion selectively to distance the first jaw from the second jaw, wherein the adjustment mechanism comprises:
   a threaded collar captured in a slot in the second body portion; and
   a threaded rod received through the threaded collar;
   wherein the first body portion is coupled to the threaded rod via a biasing element, wherein the biasing element biases the first jaw away from the second jaw; and
   a manually operable locking mechanism, separate from the adjustment mechanism, to lock the first body portion with respect to the second body portion selectively to prevent movement of the first jaw with respect to the second jaw against the action of the biasing element.

2. The unicondylar balancer of claim 1, further comprising a plurality of first markings located on the first and second body portions for reading off a distance between a femoral condyle contacting surface of the first jaw and a tibial plateau contacting surface of the second jaw.

3. The unicondylar balancer of claim 1, further comprising a plurality of second markings for reading off a force applied between the first jaw and the second jaw by the biasing element.

4. The unicondylar balancer of claim 1, further comprising a shaft extending substantially parallel to the threaded rod, wherein the shaft is affixed to or integral with the threaded rod, and wherein the shaft is slideably mounted through an aperture in the first body portion.

5. The unicondylar balancer of claim 4, wherein the biasing element comprises a helical spring mounted on said shaft, wherein a first end of the helical spring abuts a surface of the first body portion at a periphery of the aperture, and wherein a second end of the helical spring abuts a surface of the threaded rod.

6. The unicondylar balancer of claim 5, wherein the shaft extends from a first end of the threaded rod, and wherein the second end of the helical spring abuts the first end of the threaded rod at a periphery of said shaft.

7. The unicondylar balancer of claim 5, wherein the threaded rod has a blind axial bore having an opening at a first end of the threaded rod, wherein the shaft extends from a base of the blind axial bore, and wherein the helical spring abuts the base of the blind axial bore at a periphery of said shaft.

8. The unicondylar balancer of claim 4, where the manually operable locking mechanism comprises:

a threaded bore in the first body portion; and a threaded screw received within the threaded bore, wherein the threaded screw is rotatable within the threaded bore to move between:

a locked position in which an end of the threaded screw urges against said shaft to prevent movement of the first body portion relative to said shaft; and an unlocked position, in which said end of the threaded screw does not contact the shaft.

9. The unicondylar balancer of claim 8, wherein the threaded rod of the adjustment mechanism has a longitudinal axis, and the threaded bore has a longitudinal axis that extends perpendicular to the longitudinal axis of the threaded rod.

10. The unicondylar balancer of claim 4, wherein the manually operable locking mechanism comprises a lever located on the second body portion, wherein the lever is manually rotatable between:

a locked position in which an end of the lever is engaged with the first body portion to prevent movement of the first body portion relative to the second body portion; and an unlocked position, in which the end of the lever is disengaged from the first body portion.

11. The unicondylar balancer of claim 10, wherein the lever is pivotably mounted on the second body portion.

12. The unicondylar balancer of claim 10, wherein the lever is integral with the second body portion.

13. The unicondylar balancer of claim 10, wherein the lever comprises a concave surface for aiding manual location and operation of the lever.

14. The unicondylar balancer of claim 10, comprising two said levers located on opposite lateral sides of the second body portion.

15. The unicondylar balancer of claim 10, wherein:

the first body portion includes a laterally extending protrusion, the second body portion includes a slot extending parallel to the threaded rod, and the end of the lever is engaged with the laterally extending protrusion when in the locked position.

16. The unicondylar balancer of claim 1, further comprising a guide removably mountable on the second body portion, wherein the guide comprises:

at least two pin holes for attaching the guide to the femur.

17. The unicondylar balancer of claim 16, further comprising a cutting guide, wherein the cutting guide comprises:

a cutting guide surface; and at least two pin holes for attaching the cutting guide to the femur, wherein a spacing and orientation of the pin holes substantially matches a spacing and orientation of the pin holes of the guide.

18. The unicondylar balancer of claim 16, wherein the guide is a cutting guide comprising a cutting guide surface.

19. A method of knee surgery, the method comprising:

using a unicondylar balancer, comprising:

a first body portion including a first jaw for contacting a femoral condyle of a patient;

a second body portion slideably attached to the first body portion, the second body portion comprising second jaw for contacting a tibial plateau of the patient;

an adjustment mechanism for moving the first body portion relative to the second body portion selectively to distance the first jaw from the second jaw, wherein the adjustment mechanism comprises:

a threaded collar captured in a slot in the second body portion; and a threaded rod received through the threaded collar;

wherein the first body portion is coupled to the threaded rod via a biasing element, wherein the biasing element biases the first jaw away from the second jaw; and a manually operable locking mechanism, separate from the adjustment mechanism, to lock the first body portion with respect to the second body portion selectively to prevent movement of the first jaw with respect to the second jaw against the action of the biasing element, by:

placing a leg of the patient in a flexion position;

inserting the first and second jaws between a tibial plateau and a selected femoral condyle of the leg, the selected femoral condyle being only one of a medial femoral condyle and lateral femoral condyle of the leg;

operating the adjustment mechanism to move the first body portion relative to the second body portion to distract the femoral condyle from the tibial plateau until an applied force between the first jaw and the second jaw by the biasing element reaches a desired force;

determining a distance between the selected femoral condyle contacting surface of the first jaw and the tibial plateau contacting surface of the second jaw at said desired force;

placing the leg in extension;

inserting the first and second jaws between the selected femoral condyle and the tibial plateau of the leg;

operating the adjustment mechanism to move the first body portion relative to the second body portion to distract the selected femoral condyle from the tibial plateau until an applied force between the first jaw and the second jaw by the biasing element reaches the desired force;

determining a distance between the selected femoral condyle contacting surface of the first jaw and the tibial plateau contacting surface of the second jaw at said desired force; and determining a position of a resection plane in the femur based on the distances read off using the plurality of first markings in the flexion position and the extension position.

20. The method of clause claim 19, wherein determining that the force applied between the first jaw and the second jaw by the biasing element in the flexion position and/or the extension position has reached the desired force comprises manually moving the unicondylar balancer in a direction perpendicular to the applied force, to receive tactile feedback regarding frictional forces applied to the jaws by the femoral condyle and the tibial plateau.

\* \* \* \* \*